(12) United States Patent
Park et al.

(10) Patent No.: US 11,064,958 B2
(45) Date of Patent: Jul. 20, 2021

(54) X-RAY IMAGING APPARATUS AND CONTROL METHOD THEREOF

(71) Applicant: Samsung Electronics Co., Ltd, Suwon-si (KR)

(72) Inventors: Min Cheol Park, Bucheon-si (KR); Jong Ha Lee, Hwaseong-si (KR); Dong Wook Kim, Yongin-si (KR); Eun Mi Jung, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 132 days.

(21) Appl. No.: 15/879,352

(22) Filed: Jan. 24, 2018

(65) Prior Publication Data

US 2018/0206803 A1    Jul. 26, 2018

(30) Foreign Application Priority Data

Jan. 25, 2017  (KR) ........................ 10-2017-0012211

(51) Int. Cl.
*A61B 6/00* (2006.01)
*G21K 1/10* (2006.01)

(52) U.S. Cl.
CPC .......... *A61B 6/4035* (2013.01); *A61B 6/4464* (2013.01); *A61B 6/46* (2013.01);
(Continued)

(58) Field of Classification Search
CPC ......... A61B 6/461; A61B 6/462; A61B 6/463; A61B 6/464; A61B 6/465; A61B 6/40; A61B 6/00; A61B 6/405; A61B 6/44
See application file for complete search history.

(56) References Cited

U.S. PATENT DOCUMENTS

| | | |
|---|---|---|
| 5,923,724 A | 7/1999 | Soukal |
| 6,292,537 B1 | 9/2001 | Zimmermann |

(Continued)

FOREIGN PATENT DOCUMENTS

| | | |
|---|---|---|
| JP | 2003203797 A | 7/2003 |
| JP | 2006043144 A | 2/2006 |

(Continued)

OTHER PUBLICATIONS

European Search Report dated Jun. 29, 2018 in connection with European Patent Application No. 18 15 2325.

(Continued)

*Primary Examiner* — David P Porta
*Assistant Examiner* — Mamadou Faye

(57) ABSTRACT

The present disclosure provides an X-ray imaging apparatus and control method thereof, for guiding the user to intuitively recognize an actual dose of X-rays and select a proper dose, ultimately a condition for low dose of X-ray irradiation by providing the user with information about an actual X-ray dose to which an X-ray filter effect is reflected. In accordance with an aspect of the disclosure, an X-ray imaging apparatus includes: an X-ray source configured to generate and irradiate X-rays according to an X-ray irradiation condition including at least one of a tube voltage, a tube current, or a filter; a display configured to provide a graphic user interface to receive a choice about the X-ray irradiation condition; and a controller configured to obtain a parameter that represents a dose of radiation, to which an influence of the filter is reflected, based on the selected X-ray irradiation condition and control the display to display the parameter.

13 Claims, 21 Drawing Sheets

(52) U.S. Cl.
CPC ............... *A61B 6/461* (2013.01); *A61B 6/54* (2013.01); *A61B 6/542* (2013.01); *A61B 6/545* (2013.01); *G21K 1/10* (2013.01)

(56) References Cited

U.S. PATENT DOCUMENTS

| | | |
|---|---|---|
| 2003/0138079 A1 | 7/2003 | Schmitt |
| 2012/0314834 A1* | 12/2012 | Yao .................. G01N 23/046 378/5 |
| 2014/0140477 A1 | 5/2014 | Richard et al. |
| 2015/0071407 A1* | 3/2015 | Watanabe .............. A61B 6/542 378/62 |
| 2015/0141813 A1* | 5/2015 | Kalafut ................ A61B 6/032 600/425 |
| 2015/0157284 A1 | 6/2015 | Kim et al. |
| 2015/0250440 A1 | 9/2015 | Sugahara et al. |
| 2017/0172535 A1 | 6/2017 | Kim |

FOREIGN PATENT DOCUMENTS

| | | |
|---|---|---|
| JP | 2015228928 A | 12/2015 |
| KR | 10-2015-0065376 A | 6/2015 |
| KR | 10-2015-0142544 A | 12/2015 |
| WO | 2015/111925 A1 | 7/2015 |

OTHER PUBLICATIONS

European Patent Office, "Communication pursuant to Article 94(3) EPC," Application No. EP18152325.9, dated Sep. 26, 2019, 16 pages.

Summons to attend oral proceedings pursuant to Rule 115(1) EPC dated May 12, 2021 in connection with European Patent Application No. 18 152 325.9, 4 pages.

\* cited by examiner

| IRRADIATION CONDITION | | | ACTUAL DOSE (ESE) |
|---|---|---|---|
| TUBE VOLTAGE | FILTER | AMOUNT OF TUBE CURRENT | |
| 80kVp | None | 10.0mAs | 0.72mGy |
| 83kVp | None | 8.0mAs | 0.62mGy (−14%) |
| 76kVp | Cu 0.1mm | 16.0mAs | 0.55mGy (−24%) |

X-RAY IMAGING APPARATUS AND CONTROL METHOD THEREOF

CROSS-REFERENCE TO RELATED APPLICATION

The present application is related to and claims priority to and the benefit of a Korean Patent Application No. 10-2017-0012211 filed on Jan. 25, 2017, the disclosure of which is incorporated herein by reference in its entirety.

TECHNICAL FIELD

The present disclosure relates to an X-ray imaging apparatus and control method thereof.

BACKGROUND

X-ray imaging apparatuses are devices for allowing the user to see an internal structure of a subject by irradiating X-rays to the subject and analyzing X-rays that have passed through the subject. X-ray transmittance is different depending on the tissue of a subject, so the internal structure of the subject may be imaged using an attenuation coefficient quantified from the X-ray transmittance.

A condition for X-ray irradiation used in X-raying is an important factor in determining X-ray image quality and amount of radiation exposure. Accordingly, it is important to provide proper information about the X-ray irradiation condition for the user, such as a radiological technologist, a doctor, etc.

SUMMARY

To address the above-discussed deficiencies, it is a primary object to provide an X-ray imaging apparatus and control method thereof, for guiding the user to intuitively recognize an actual dose of X-rays and select a proper dose, ultimately a condition for low dose of X-ray irradiation by providing the user with information about an actual X-ray dose to which an X-ray filter effect is reflected.

In accordance with an aspect of the disclosure, an X-ray imaging apparatus comprises: an X-ray source configured to generate and irradiate X-rays according to an X-ray irradiation condition including at least one of a tube voltage, a tube current, exposure time, or a filter; a display configured to provide a graphic user interface to receive a choice about the X-ray irradiation condition; and a controller configured to obtain a parameter that represents a dose of radiation, to which an influence of the filter is reflected, based on the selected X-ray irradiation condition and control the display to display the parameter.

The parameter that represents a dose of radiation to which an influence of the filter is reflected may comprise at least one of an amount of tube current corresponding to X-rays that have transmitted the filter, a dose of X-rays that have transmitted the filter, or a ratio of a dose of X-rays that have not transmitted the filter and a dose of X-rays that have transmitted the filter.

The display may be configured to display the parameter in a numerical value, or a diagram or image representing the numerical value.

The X-ray imaging apparatus may further comprise a storage configured to store relationships between dose per amount of tube current (mAs) and tube voltage by differing types or thickness of the filter.

The controller may be configured to search the storage for a dose per amount of tube current corresponding to the selected X-ray irradiation condition, when the choice of the X-ray irradiation condition is input.

The controller may be configured to additionally search for a dose per amount of tube current corresponding to an occasion when no filter is used in the selected X-ray irradiation condition.

The controller may be configured to obtain a ratio of a dose of X-rays that have not transmitted the filter and a dose of X-rays that have transmitted the filter, based on a dose per amount of tube current corresponding to the selected X-ray irradiation condition and a dose per amount of tube current corresponding to an occasion when the filter is not used in the selected X-ray irradiation condition.

The controller may be configured to obtain an amount of tube current corresponding to X-rays that have transmitted the filter based on the obtained ratio and the amount of tube current included in the selected X-ray irradiation condition.

The controller may be configured to obtain a dose of X-rays that have transmitted the filter based on a dose per amount of tube current corresponding to the selected X-ray irradiation condition and an amount of tube current included in the selected X-ray irradiation condition.

The controller may be configured to when at least one of an imaging protocol or a size of a subject is selected, control the display to display a basic X-ray irradiation condition corresponding to the selected at least one of the imaging protocol or the size of the subject.

The controller may be configured to obtain a parameter that represents a dose to which an influence of the filter is reflected based on the basic X-ray irradiation condition.

The controller may be configured to re-obtain a parameter that represents a dose of radiation, to which an influence of the filter is reflected, whenever a choice of the X-ray irradiation condition is changed, and control the display to display the parameter.

In accordance with an aspect of the disclosure, a control method of an X-ray imaging apparatus, the method comprising: providing a graphic user interface configured to receive a choice of an X-ray irradiation condition including at least one of a tube voltage, a tube current, exposure time, or a filter; obtaining a parameter that represents a dose to which an influence of the filter is reflected based on the selected X-ray irradiation condition; and displaying the obtained parameter on a display.

The parameter that represents a dose of radiation to which an influence of the filter is reflected may comprise at least one of an amount of tube current corresponding to X-rays that have transmitted the filter, a dose of X-rays that have transmitted the filter, or a ratio of a dose of X-rays that have not transmitted the filter and a dose of X-rays that have transmitted the filter.

The displaying of the obtained parameter on a display may comprise displaying the parameter in a numerical value, or a diagram or image representing the numerical value.

The method may further comprise storing relationships between dose per amount of tube current (mAs) and tube voltage by differing types or thickness of the filter in a storage.

The obtaining of a parameter that represents a dose to which an influence of the filter is reflected may comprise searching the storage for a dose per amount of tube current corresponding to the selected X-ray irradiation condition, when the choice of the X-ray irradiation condition is input.

The obtaining of a parameter that represents a dose to which an influence of the filter is reflected may comprise searching for a dose per amount of tube current corresponding to an occasion when no filter is used in the selected X-ray irradiation condition.

The obtaining of a parameter that represents a dose to which an influence of the filter is reflected may comprise obtaining a ratio of a dose of X-rays that have not transmitted the filter and a dose of X-rays that have transmitted the filter, based on a dose per amount of tube current corresponding to the selected X-ray irradiation condition and a dose per amount of tube current corresponding to an occasion when the filter is not used in the selected X-ray irradiation condition.

The obtaining of a parameter that represents a dose to which an influence of the filter is reflected may comprise obtaining an amount of tube current corresponding to X-rays that have transmitted the filter based on the obtained ratio and the amount of tube current included in the selected X-ray irradiation condition.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIG. 9 illustrates an example of a screen displayed on a display of an X-ray imaging apparatus, according to an embodiment of the present disclosure;

FIG. 10 illustrates a table representing radiation doses depending on X-ray irradiation conditions;

FIGS. 12 to 18 illustrate examples in which an X-ray imaging apparatus in accordance with an embodiment displays information about radiation doses on a display, to which an influence of a filter is reflected;

DETAILED DESCRIPTION

Figure 1:
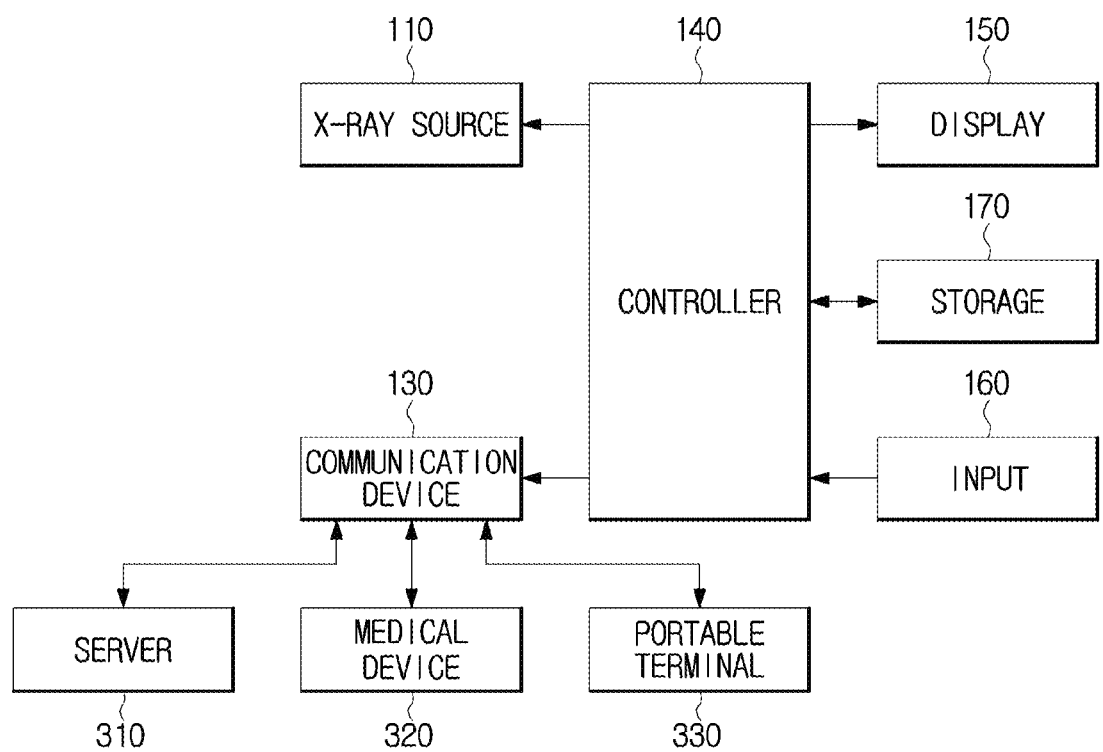
FIG. 1 illustrates a control block diagram of an X-ray imaging apparatus, according to an embodiment of the present disclosure.

FIGS. 1 through 21, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

Embodiments and features as described and illustrated in the present disclosure are only preferred examples, and various modifications thereof may also fall within the scope of the disclosure.

The terminology used herein is for the purpose of describing particular embodiments only and is not intended to limit the present disclosure.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section.

It is to be understood that the singular forms "a," "an," and "the" include plural references unless the context clearly dictates otherwise.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Furthermore, the terms, such as "~ part", "~ block", "~ member", "~ module", etc., may refer to a unit of handling at least one function or operation. For example, the terms may refer to at least one process handled by hardware such as field-programmable gate array (FPGA)/application specific integrated circuit (ASIC), etc., software stored in a memory, or at least one processor.

Reference numerals used for method steps are just used for convenience of explanation, but not to limit an order of the steps. Thus, unless the context clearly dictates otherwise, the written order may be practiced otherwise.

Embodiments of the present disclosure will now be described with reference to accompanying drawings. Throughout the drawings, like reference numerals may refer to like parts or components.

Figure 2:
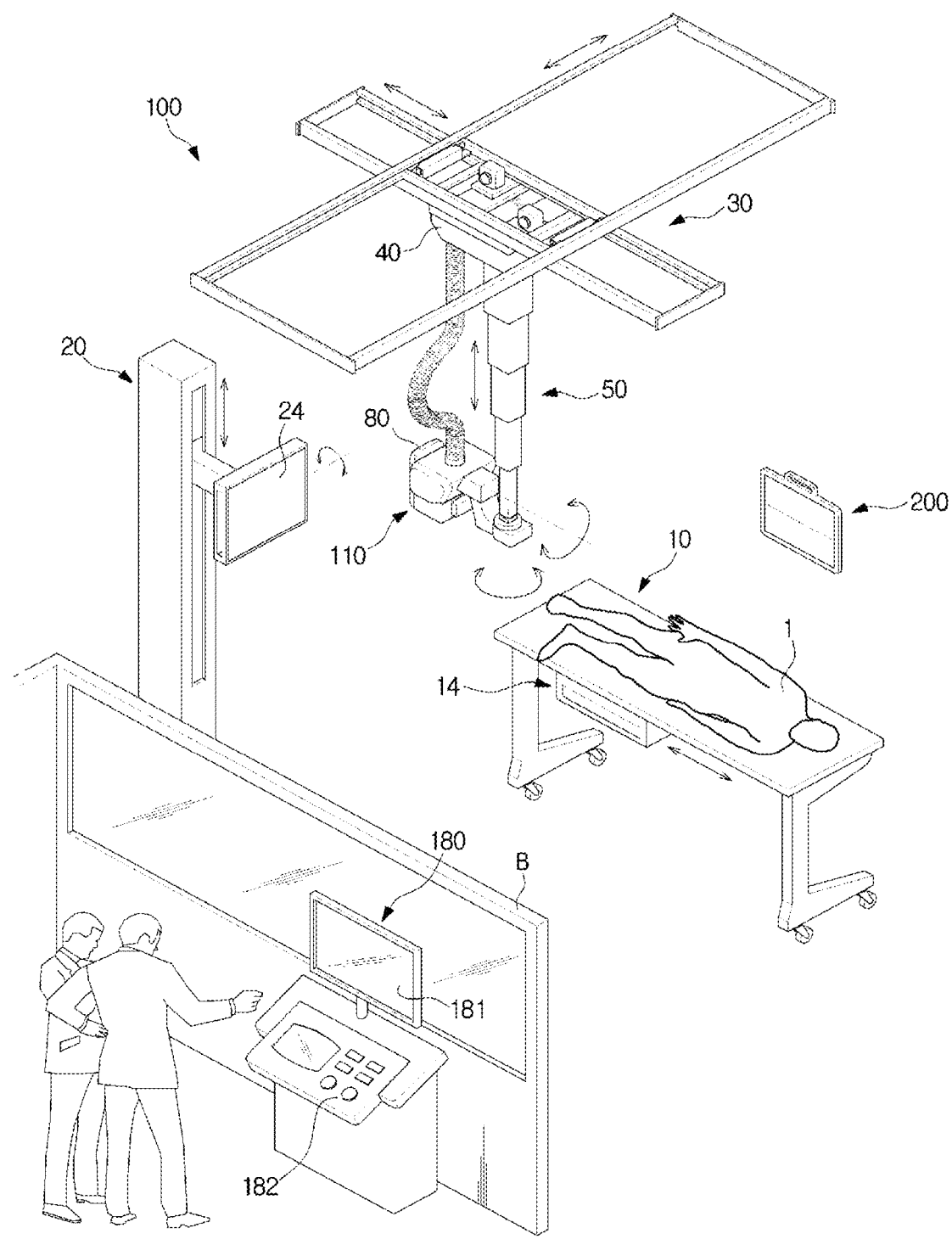
FIG. 2 illustrates an external view illustrating a configuration of and X-ray imaging apparatus, according to an embodiment of the present disclosure.
Figure 3:
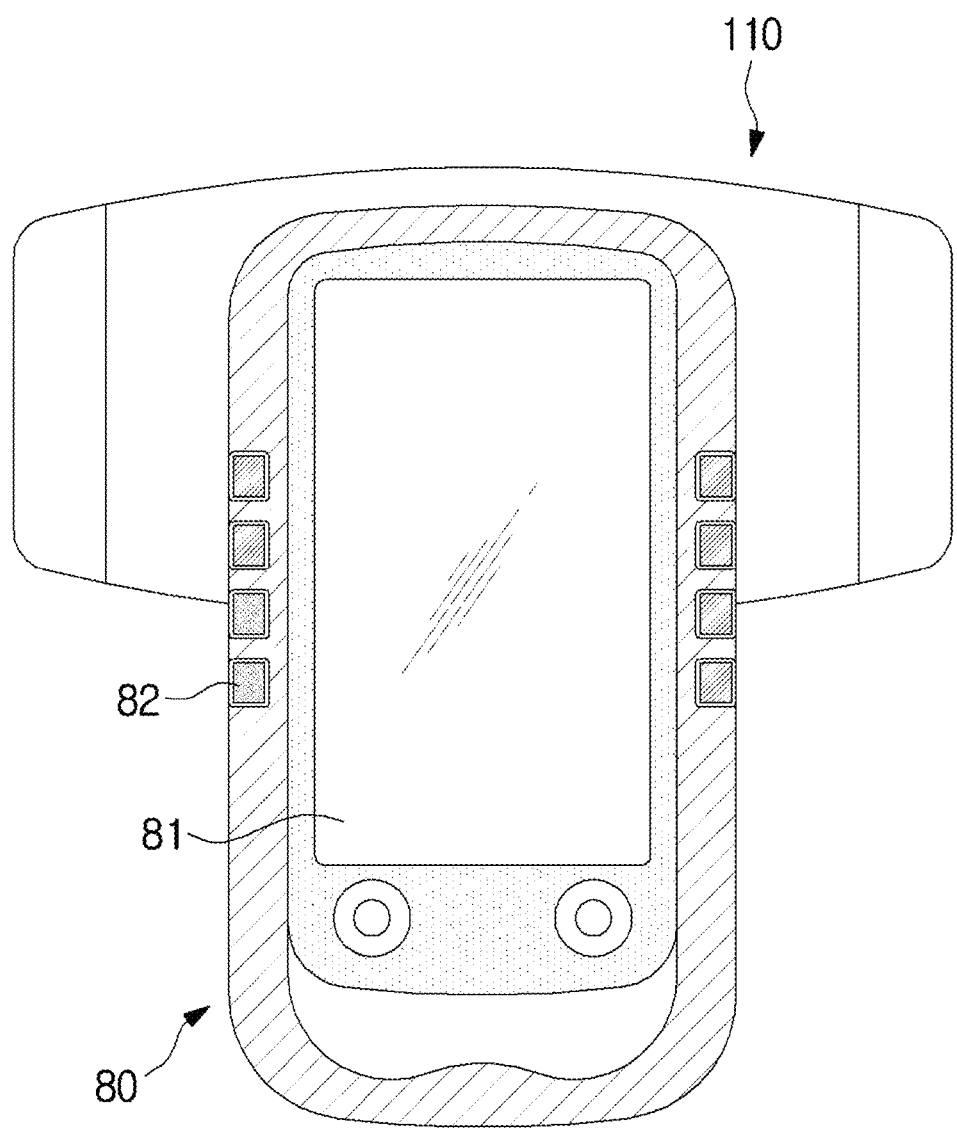
FIG. 3 illustrates an exterior view of a sub-display device equipped in an X-ray source.

FIG. 1 illustrates a control block diagram of an X-ray imaging apparatus, according to an embodiment of the present disclosure, FIG. 2 illustrates an external view illustrating a configuration of X-ray imaging apparatus, according to an embodiment of the present disclosure, and FIG. 3 illustrates an exterior view of a sub-display device equipped in an X-ray source. FIG. 2 shows an example of an X-ray imaging apparatus, which is a ceiling type X-ray imaging apparatus with an X-ray source attached to the ceiling of an examination room.

Referring to FIG. 1, an X-ray imaging apparatus 100 in accordance with an embodiment may include an X-ray source 110 for generating and irradiating X-rays, a display 150 for displaying a screen e.g., to set an X-ray irradiation condition, an input 160 for receiving control commands including a command to set an X-ray irradiation condition from the user, a storage 170 for storing e.g., information about an X-ray irradiation condition, and a controller 140 for controlling overall operation of the X-ray imaging apparatus 100.

The X-ray imaging apparatus 100 may further include a communication device 130 for communicating with an external device.

The controller 140 may control X-ray irradiation timing, X-ray irradiation conditions, and the like, of the X-ray source 110 according to a command entered by the user, and create an X-ray image using data received from an X-ray detector 200 (see FIG. 2).

The controller 140 may also control a position or posture of an install portion 14, 24 in which the X-ray source 110 or the X-ray detector 200 is installed, according to an X-raying protocol and a position of a subject 1.

The controller 140 may compute a parameter that represents a dose of radiation to which an influence of a filter is reflected based on a selected X-ray irradiation condition, and control the display 150 to display the parameter.

The parameter that represents a dose to which an influence of a filter is reflected may include at least one of an amount of tube current corresponding to X-rays that have transmitted the filter, a dose of X-rays that have transmitted the filter, and a ratio of a dose of X-rays that have not transmitted the filter and a dose of X-rays that have transmitted the filter.

The controller 140 may include a memory for storing a program for carrying out the aforementioned operations and the following operations, and a processor for executing the program. The controller 140 may include a single processor or multiple processors, and in the latter case, the multiple processors may be integrated in a single chip or may be physically separated.

When the controller 140 includes the multiple processors and multiple memories, some of the multiple processors and memories may be included in a workstation 180 (see FIG. 2), and some others in a sub-display 80 (see FIG. 2), a moving carriage 40 (see FIG. 2), or other device.

For example, the processor(s) included in the workstation 180 may perform control, such as image processing to create an X-ray image, and the processor(s) included in the sub-display 80 or the moving carriage 40 may perform control over the movement of the X-ray source 110 or the X-ray detector 200.

The X-ray imaging apparatus 100 may be connected to an external device (e.g., an external server 310, another medical device 320, and a portable terminal 330, such as a smart phone, a tablet Personal Computer (PC), a wearable device, and the like) through the communication device 130 for exchanging data.

The communication device 130 may include one or more components that enable communication with an external device, for example, at least one of a short-range communication module, a wired communication module, and a wireless communication module.

The communication module 130 may further include an internal communication module to enable communication between components of the X-ray imaging apparatus 100.

The communication device 130 may also receive a control signal from the external device and forward the control signal for the controller 140 to control the X-ray imaging apparatus 100 according to the control signal.

Furthermore, the controller 140 may control an external device with a control signal of the controller 140 by sending the control signal to the external device through the communication device 130.

For example, the external device may process data of its own according to the control signal received from the controller 140 through the communication device 130. The external device may have a program to control the X-ray imaging apparatus 100, and the program may include instructions to control some or the entire operation of the controller 140.

In the portable terminal 330, the program may be installed in advance or by being downloaded by the user from a server that provides applications. The server that provides applications may include a recording medium that stores the program.

Referring to FIG. 2, a guide rail 30 may be installed on the ceiling of the examination room where the X-ray imaging apparatus 100 is placed, and the X-ray source 110 linked to a moving carriage 40 that moves along the guide rail 30 may be moved to a position corresponding to the subject 1, and the moving carriage 40 and the X-ray source 110 may be linked through a foldable post frame 50 to adjust the altitude of the X-ray source 110 from the ground.

The X-ray source 110 may be moved automatically or manually. In the former case, the X-ray imaging apparatus 100 may further include a driver, such as a motor to provide power to move the X-ray source 110.

The workstation 180 may be provided in the space separated by a blackout curtain B from the space where the X-ray source 110 is placed. The workstation 180 may be equipped with an input 182 for receiving commands from the user and a display 181 for displaying information.

The input 182 may receive commands to control an imaging protocol, select an X-ray irradiation condition or X-ray irradiation timing, control a position of the X-ray source 110, and the like. The input 182 may include a keyboard, a mouse, a touch screen, a voice recognizer, and so forth.

The display 181 may display screens representing an image for guiding input of the user, an X-ray image, and/or a state of the X-ray imaging apparatus 100.

In the meantime, the display 150 and the input 160 as described in connection with FIG. 1 may be implemented as the display 181 and the input 182 provided in the workstation 180, or as sub-display 81 and a sub-input 82 provided in the sub-display 80, or a display and an input provided in the portable terminal 330, such as a tablet PC or a smart phone.

The X-ray detector 200 may be implemented as a fixed type of X-ray detector fixed on a stand 20 or a table 10, or may detachably equipped in the install portion 14, 24. Alternatively, the X-ray detector 300 may be implemented as a portable X-ray detector available at any place. The portable X-ray detector may further be classified into a wired type or a wireless type depending on the data transfer method or the power supplying method.

The X-ray detector 200 may also be moved automatically or manually. In the former case, the X-ray imaging apparatus 100 may further include a driver, such as a motor to provide power to move the install portion 14, 24.

The X-ray detector 200 may or may not be included as an element of the X-ray imaging apparatus 100. In the latter case, the X-ray detector 200 may be registered in the X-ray imaging apparatus 100 by the user. In both cases, the X-ray detector 200 may be connected to the controller 140 through the communication device 130 for receiving a control signal or sending image data.

The sub-display 80 may be arranged on one side of the X-ray source 110 to provide information for the user and receive a command from the user, and may perform a part or all of the functions performed by the input 182 and the display 181 of the workstation 180.

If all or part of the components of the controller 140 and the communication device 130 are provided separately from the workstation 180, they may be included in the sub-display 80 arranged on the X-ray source 110.

The user may input various kinds of information or commands relating to X-raying in a way of manipulating the sub-input 82 or touching the sub-display 81 as shown in FIG. 3.

For example, the user may input a position to be moved by the X-ray source 110 through the sub-input 82 or the sub-display 81.

While FIG. 2 illustrates a fixed type of X-ray imaging apparatus attached onto the ceiling of an examination room, the X-ray imaging apparatus 100 may include any of different types of X-ray imaging apparatus, such as a C-arm type of X-ray imaging apparatus, a mobile X-ray imaging apparatus, and the like, within the scope of the present disclosure obvious to ordinary people in the art.

The X-ray source 110 may be equipped with an X-ray tube for generating X-rays and a collimator for adjusting an irradiation range of X-rays generated by the X-ray tube. The X-ray source 110 may also be called a tube head unit (THU) because X-ray source 110 includes an X-ray tube. This will be explained in detail below.

Figure 4:
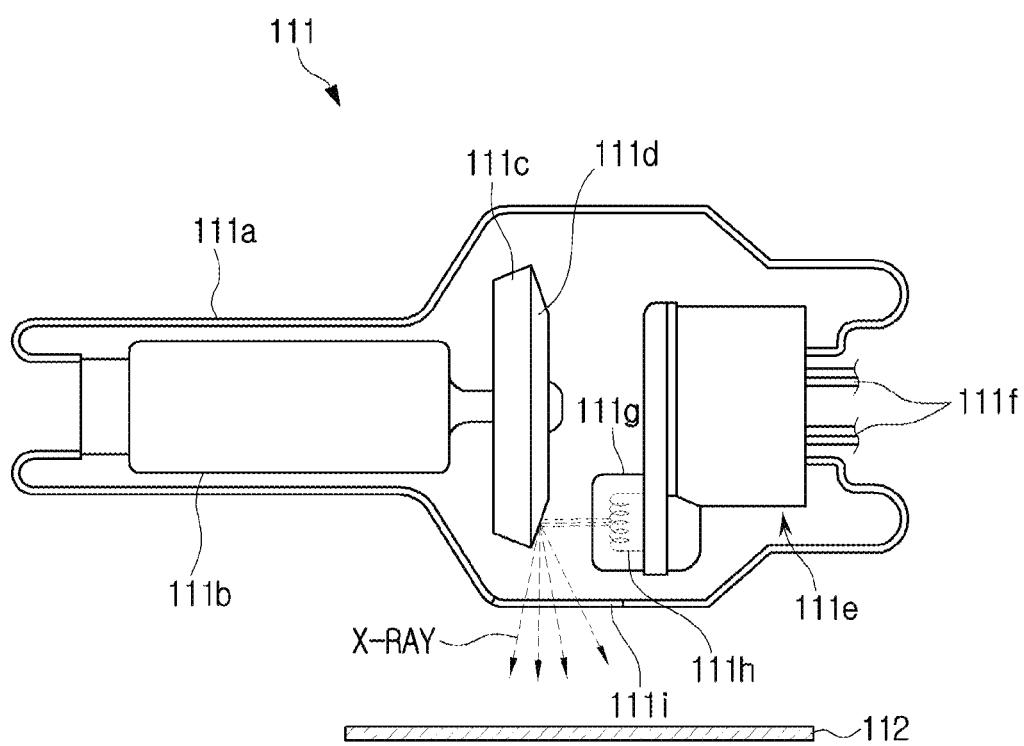
FIG. 4 illustrates a side cross-sectional view schematically illustrating a structure of an X-ray tube included in an X-ray source.

FIG. 4 is a side cross-sectional view schematically illustrating a structure of an X-ray tube included in an X-ray source.

The X-ray source 110 may include an X-ray tube 111 as shown in FIG. 4. The X-ray tube 111 may be implemented by a 2-pole vacuum tube with positive and negative electrodes. For example, thermions may be generated by making the inside of a glass tube 111*a* in a high vacuum state and heating a filament 111*h* of a negative electrode 111*e* to a high temperature.

The negative electrode 111*e* may include the filament 111*h* and a focusing electrode 111*g* that focuses electrons, the focusing electrode 111*g* also called a focusing cup.

When a high voltage is applied across the positive electrode 111*b* and the negative electrode 111*e*, thermions get accelerated and collide with a target material 111*d* of the positive electrode 111*b*, thus producing X-rays. The target material 111*d* of the positive electrode 111*b* may include a high resistive material, such as Cr, Fe, Co, Ni, W, Mo, or the like.

The X-ray produced in this way is irradiated out through a window 111*i*, and the window 111*i* may use, for example, a thin film of Beryllium (Be).

The voltage applied across the positive and negative electrodes 111*b* and 111*e* is called a tube voltage, the magnitude of which may be represented in kilovolt peak (kVp). As the tube voltage increases, the speed of the thermion increases and as a result, energy of X-rays (energy of photons) produced from collision of the thermion with the target material increases.

The X-ray source 110 may irradiate X-rays with a certain energy band. The energy band of the irradiated X-rays may be defined by upper and lower limits, and the energy of the X-rays may be represented by average energy, highest energy, energy band, and the like.

A filter 112 may be arranged in a direction, toward which X-rays are irradiated, to control the X-ray energy. For this, with the filter 112 arranged on the front or back side of the window 111*i* for filtering X-rays in a particular energy band, the X-rays of the particular energy band may be filtered. The filter 112 may be called an additional filter.

The upper limit of the energy band, namely, a maximum energy of X-rays to be irradiated may be controlled by the level of the tube voltage, and the lower limit of the energy band, namely, a minimum energy of X-rays to be irradiated may be controlled by the filter. Filtering X-rays of a low energy band by means of the filter 112 may increase the average energy of X-rays to be irradiated.

For example, with the filter 112 made of aluminum or copper to filter X-rays of a low energy band which degrade the image quality, the X-ray beam quality may be hardened, thereby increasing the lower limit of the energy band. Accordingly, an average energy level of X-rays to be irradiated increases. Furthermore, filtering X-rays of a particular energy band by means of the filter 112 may decrease a dose of radiation exposure of a subject.

A current flowing through the X-ray tube 111 is called a tube current, which may be represented by an average value (mA), or represented by an amount of the tube current (mAs), which is a tube current (mA) for an X-ray exposure time (s).

As the tube current increases, the dose of X-rays (the number of X-ray photons) increases. Accordingly, the X-ray energy may be controlled by the tube voltage, and the dose of X-rays may be controlled by the tube current and the X-ray exposure time, i.e., the amount of tube current.

Figure 5:
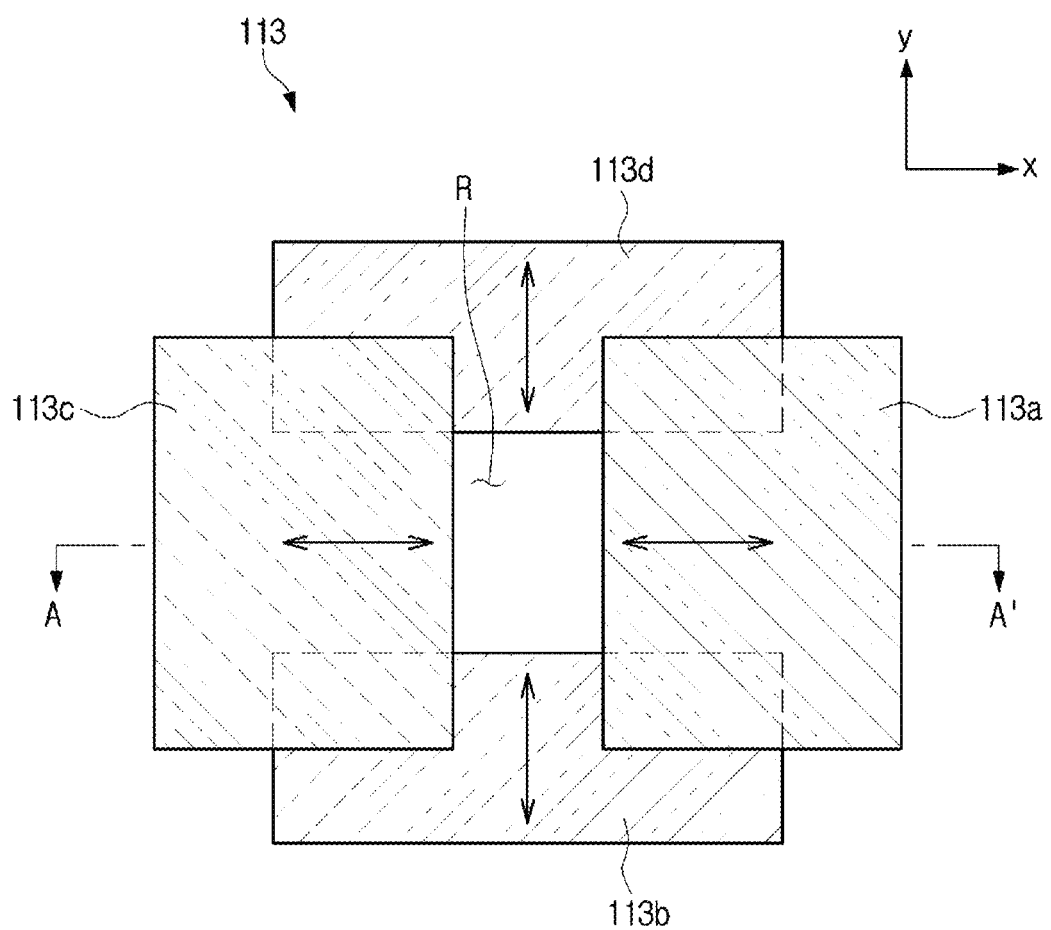
FIG. 5 illustrates a configuration of a collimator.
Figure 6:
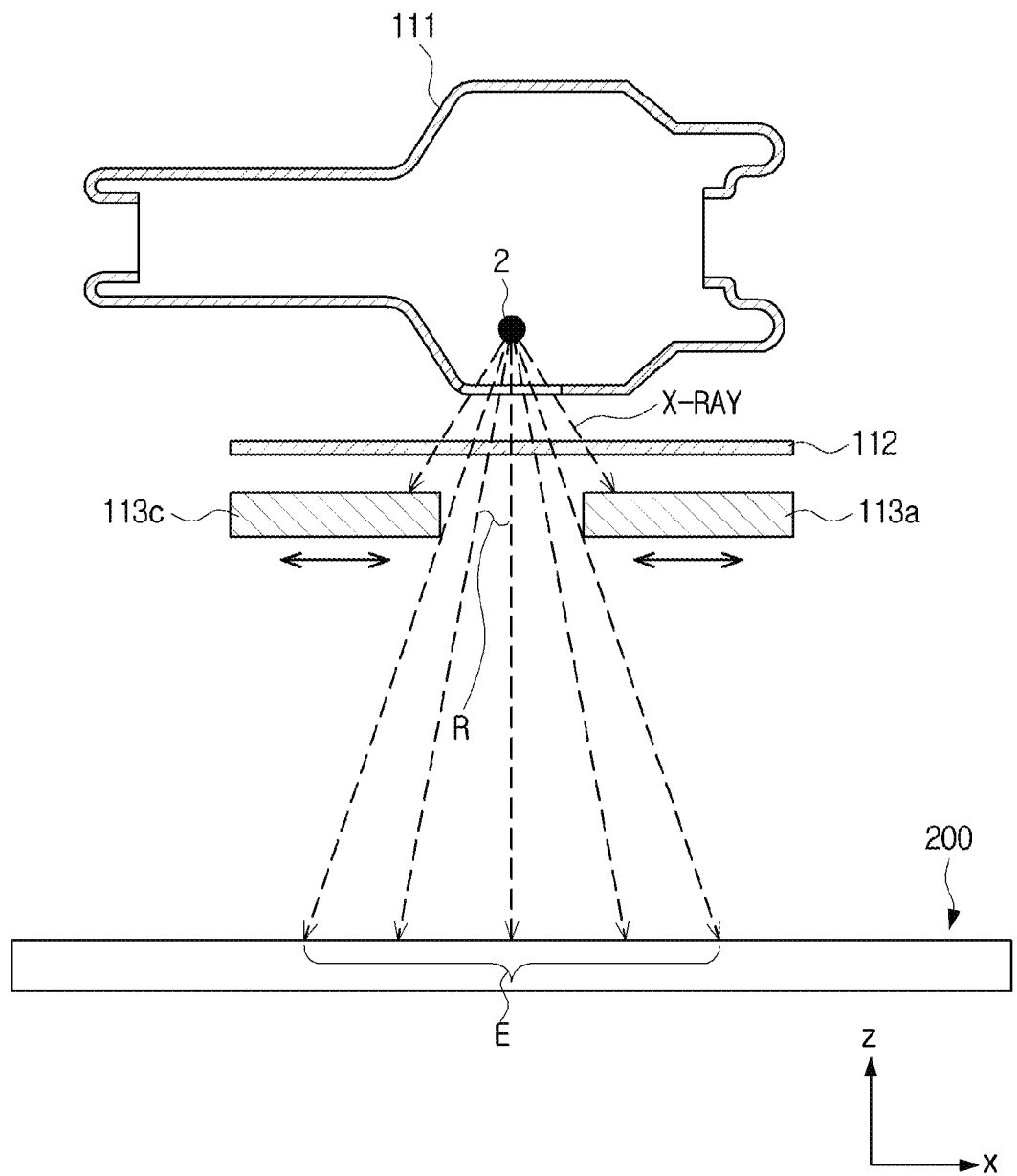
FIG. 6 illustrates a side cross-sectional view of blades cut along AA'.

FIG. 5 shows a configuration of a collimator, and FIG. 6 is a side cross-sectional view of blades cut along AA'.

Referring to FIG. 5, the collimator 113 may include at least one movable blade 113*a*, 113*b*, 113*c*, and 113*d*, and the blades 113*a*, 113*b*, 113*c*, and 113*d* may be made of a material with high bandgap to absorb X-rays.

An X-ray irradiation range may be adjusted as the blades 113*a*, 113*b*, 113*c*, and 113*d* move, and the collimator 113 may further include a motor to provide power to the respective blades.

The controller 140 calculates an extent of movement of each blade 113*a*, 113*b*, 113*c*, 113*d* corresponding to a set X-ray irradiation range, and sends the collimator 113 a control signal to move the blade 113*a*, 113*b*, 113*c*, 113*d* as far as the calculated extent of movement.

For example, the collimator 113 may include four blades 113a, 113b, 113c, and 113d, each of which has the form of a flat plate. The first blade 113a and the third blade 113c may be movable in both directions along the X-axis, and the second blade 113b and four blade 113d may be movable in both directions along the Y-axis.

Furthermore, each of the four blades 113a, 113b, 113c, and 113d may be moved individually, or the first blade 113a and the third blade 113c may be moved as one set and the second blade 113b and the fourth blade 113d may be moved as another set.

X-rays may be irradiated through a slot R formed by the four blades, and collimation may be performed by passing the X-rays through the slot R. In this embodiment, the slot R refers to a collimation range, and the X-ray irradiation range refers to an area in which X-rays that have passed the collimation range R are incident onto the subject 1 or the X-ray detector 200.

Referring to FIG. 6, the collimator 113 is arranged in front of the X-ray tube 111. The front of the X-ray tube 111 corresponds to a direction in which the X-ray is irradiated.

The filter 112 may be arranged between the blades 113a, 113b, 113c, and 113d and the X-ray tube 111.

X-rays irradiated from a focusing point 2 of the X-ray tube 111 are irradiated into an irradiation range E limited by the collimator 113, and thus scattering is reduced.

Some X-rays incident on the blade 113a, 113b, 113c, 113d among the X-rays irradiated from the X-ray tube 111 are absorbed by the blade, and some X-rays that have passed the collimation range R are incident on the X-ray detector 200. The following description will focus on an occasion when there is no subject.

If X-rays spread like cone beams, the X-ray irradiation range E is wider than the collimation range R. The controller 140 may irradiate X-rays into a desired range of X-ray irradiation range E by adjusting the collimation range R based on a relationship between the two ranges.

Although the previous example shows that the collimator 113 is equipped with four rectangular blades, it is only by way of example and there are no limitations on the number or shape of the blades included in the collimator 113.

Figure 7:
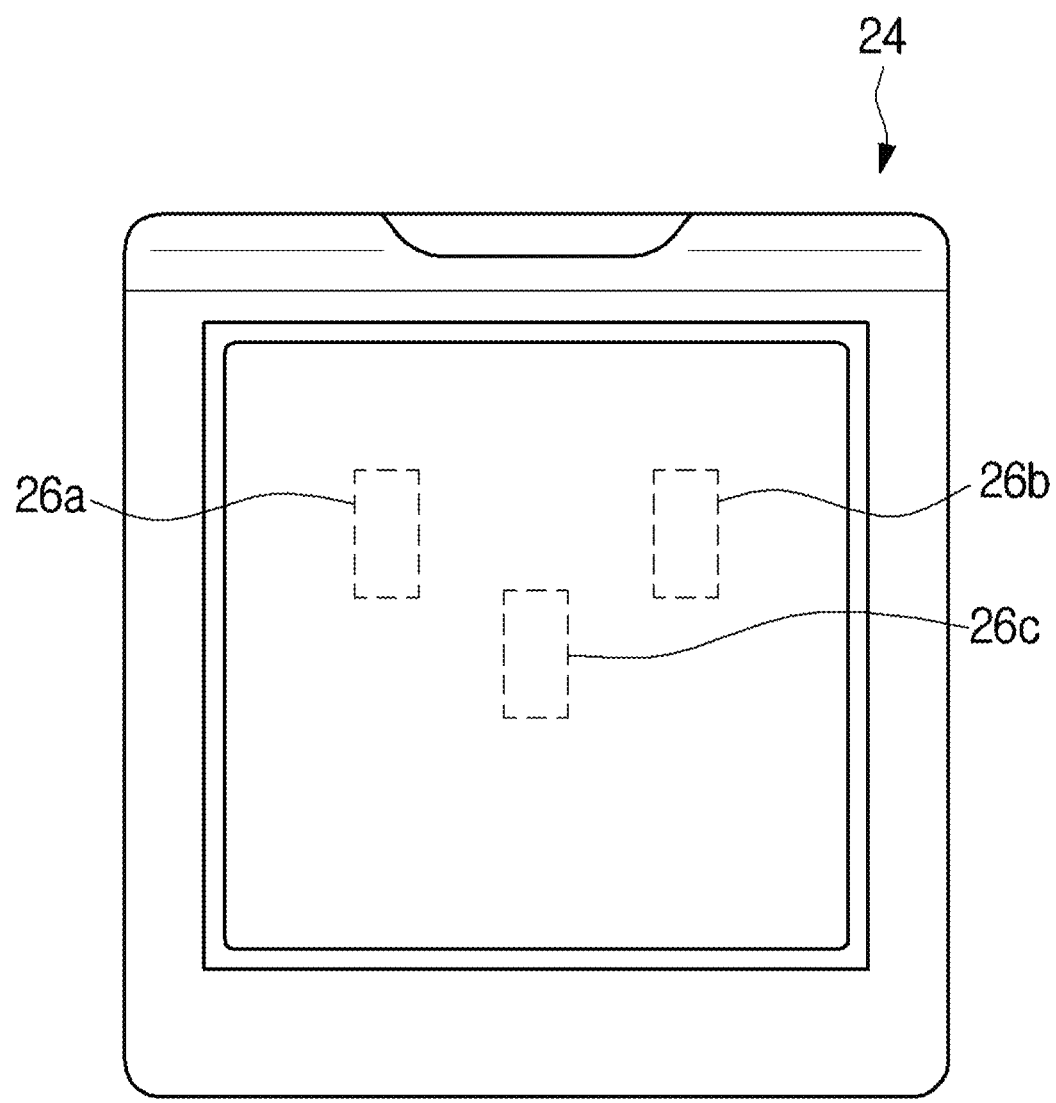
FIGS. 7 and 8 illustrate an example of automatic exposure control (AEC) sensor to be used in an X-ray imaging apparatus, according to an embodiment of the present disclosure.
Figure 8:
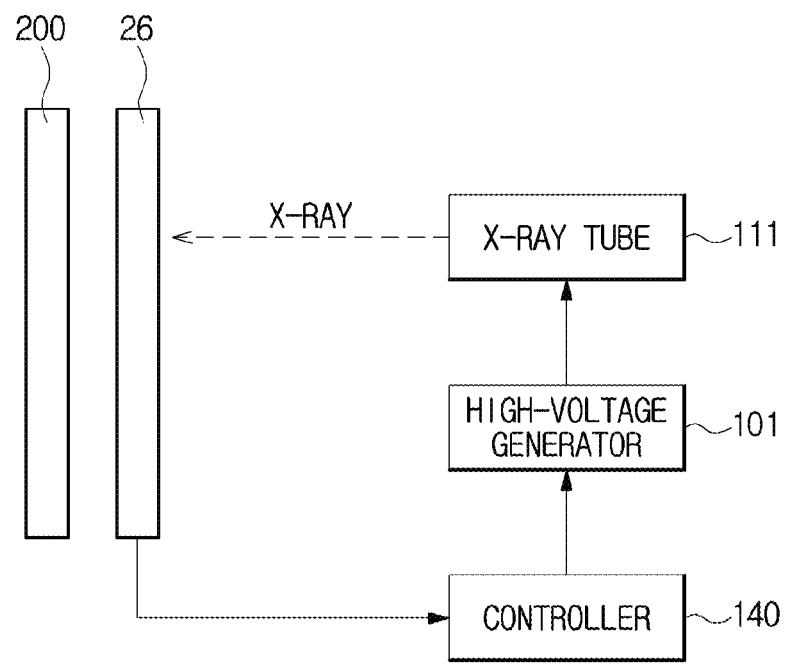

FIGS. 7 and 8 show an example of automatic exposure control (AEC) sensor to be used in an X-ray imaging apparatus, according to an embodiment of the present disclosure.

The X-ray imaging apparatus 100 may perform AEC to prevent excessive exposure of the subject to radiation. For this, as shown in FIG. 7, the install portion 24 may have an AEC sensor module 26 to detect a dose of X-rays. This embodiment will be described using the install portion 24 of the stand 20, but the AEC sensor module 26 may also be provided in the install portion 14 of the table 10.

The diagram of FIG. 7 shows the install portion 24 viewed from the front. The AEC sensor module 26 may be arranged inside the install portion 24, and may include a plurality of AEC sensors 26a, 26b, 26c for independently detecting a dose of X-rays. For example, each AEC sensor may be implemented as an ionization chamber.

Although there are total of three AEC sensors, two of them arranged on an upper portion and one arranged on a lower portion, it is only an example and it is also possible to have more than or less than three AEC sensors in different positions.

Referring to FIG. 8, the AEC sensor module 26 may be located in front of the X-ray detector 200. The front of the X-ray detector 200 corresponds to a direction in which the X-ray is incident. FIG. 8 is a side view of the AEC sensor module 26 arranged in front of the X-ray detector 200.

When X-rays are incident on the AEC sensor, a current may be induced and the AEC sensor may send a signal corresponding to the current to the controller 140. The signal to be sent to the controller 140 may be amplified and digitally processed.

The controller 140 may determine whether a current dose of the incident X-ray exceeds a threshold dose, based on the signal. If the dose of X-rays exceeds the threshold dose, a cut-off signal is sent to a high-voltage generator 101 that supplies a high voltage to the X-ray tube 111 to stop generation of the X-ray.

A grid may be arranged on the front of the AEC sensor module 26 to prevent X-ray scattering. Some of the X-rays irradiated from the X-ray source 110 may collide with dust in the air or constituent materials of the subject and scatter away from an original path on the way to the X-ray detector 200. When incident on the X-ray detector 200, the scattered X-rays give a negative influence to the quality of X-ray images, such as degradation of contrast of the X-ray image.

The grid may have a structure in which shielding materials, such as lead (Pb), which absorb X-rays, are arranged, and some of the irradiated X-rays that proceed in the original direction, that is, straightforward X-rays, may pass between the shielding materials and then be incident on the X-ray detector 200 while the scattered X-rays collide with the shielding materials and are absorbed.

The shielding materials may be arranged linearly or in a cross structure. Alternatively, the shielding materials may be arranged in a focused form by being inclined to be similar to the X-ray irradiation direction, or may be arranged to be parallel.

Although not shown, a driver including a motor to mechanically move the grid may be included inside the install portion 24. Accordingly, it is possible to control an angle or center position of the grid by sending a control signal to the driver from the outside.

Although the AEC sensor module 26 is provided in the install portion 24 in this example, the AEC sensor module 26 may be integrated with the X-ray detector 200.

Figure 9:
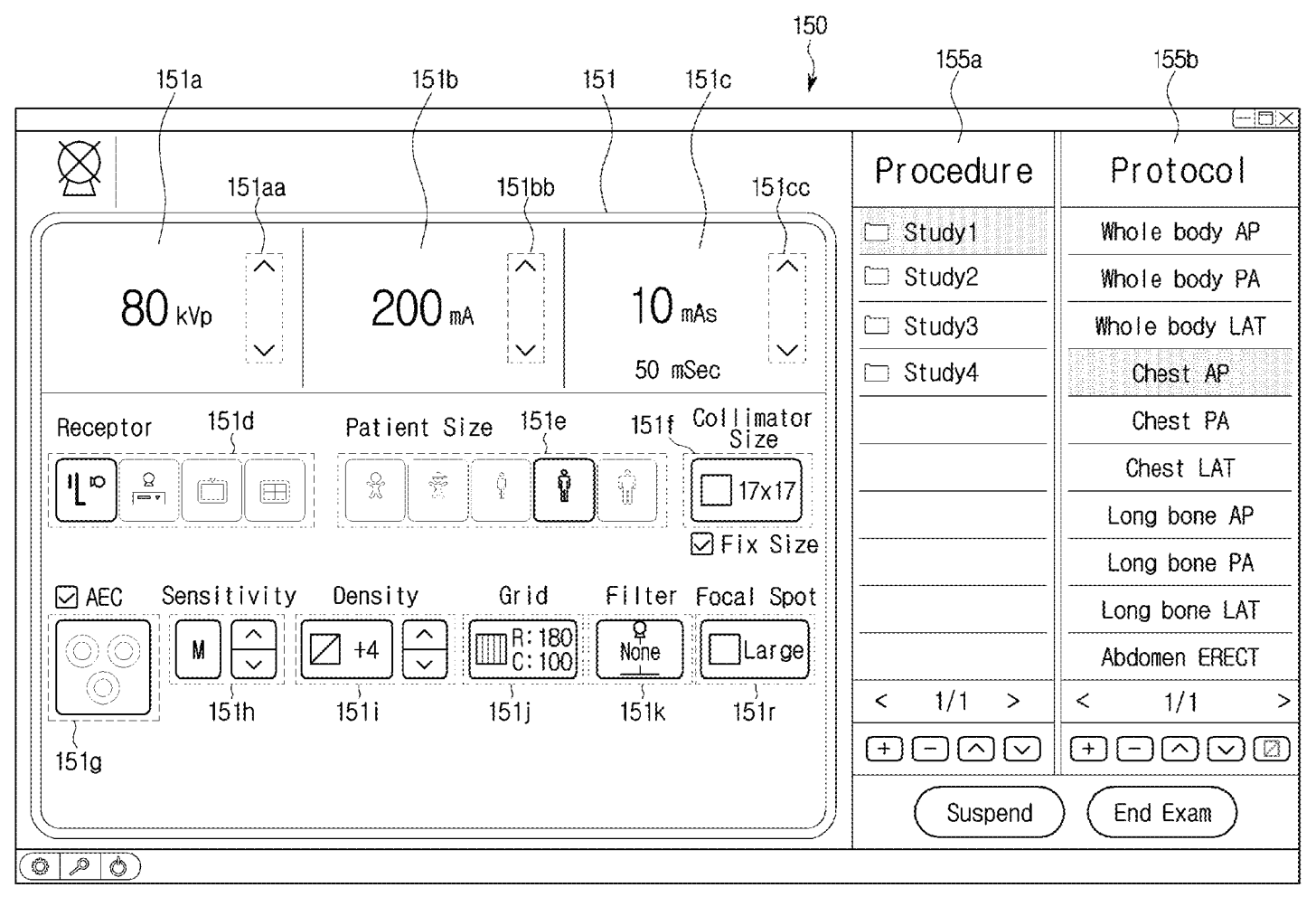

FIG. 9 shows an example of a screen displayed on a display of an X-ray imaging apparatus, according to an embodiment of the present disclosure.

Referring to FIG. 9, a setting window 151 to set an X-ray irradiation condition and a work list 155 may be displayed on the display 150.

The work list 155 may include a study list 155a to select a study and a protocol list 155b to select an imaging protocol. The term 'study' as herein used may refer to a set of X-ray images related to each other.

If a study is selected from among the study list 155a, the protocol list 155b to select an imaging protocol to be applied to the selected study is displayed.

The X-raying region may vary by imaging protocol, and a suitable X-ray irradiation condition may vary by the X-raying region. The imaging protocol may be determined based on the X-raying portion, the posture of the subject, and the like.

For example, the imaging protocol may include the whole body Anterior-Posterior (AP), the whole body Posterior-Anterior (PA), the whole body LAT. Even for the chest, there may be imaging protocols for capturing images in the AP, PA, LAT methods, and for long bones such as legs, there may be imaging protocols for capturing images in the AP, PA, LAT methods. Furthermore, Abdomen Erect may also be included in the imaging protocol.

A graphic user interface may be displayed on the setting window 151 for the user to intuitively control the X-ray imaging apparatus 100. The graphic user interface may be used to receive a choice of an X-ray irradiation condition including at least one of a tube voltage, a tube current, exposure time, and a filter.

The graphic user interface may include a plurality of graphic objects that may set various X-ray irradiation conditions.

In this embodiment, all the objects, such as buttons, icons, and the like, displayed on the display 150 to provide information or used to receive the user's control command may be called graphic objects.

The graphic objects may be implemented by buttons corresponding to the respective X-ray irradiation conditions to be used in receiving a command to set an X-ray irradiation condition from the user.

For example, they may include a tube voltage set button 151a to receive a setting of a tube voltage (kVp), a tube current set button 151b to receive a setting of a tube current (mA), and a tube current amount set button 151c to receive an amount of tube current (mAs).

The currently set tube voltage, tube current, and amount of tube current may be displayed on one side of the respective buttons. A currently set tube voltage may be displayed in a numerical value in a tube voltage display area 151aa on one side of the tube voltage set button 151a, and a currently set tube current may be displayed in a numerical value in a tube current display area 151bb on one side of the tube current set button 151b.

A currently set amount of tube current may be displayed in a numerical value in a tube current amount display area 151cc on one side of the tube current amount set button 151c. The tube current amount set button 151c may actually be used in controlling X-ray exposure time (sec) unlike the tube current set button 151b. A currently set X-ray exposure time may also be displayed in the tube current amount display area 151cc.

In some embodiments, instead of the tube current amount set button 151c, an X-ray exposure time set button may be provided separately.

The user may select each button to set an X-ray irradiation condition to a desired value. The selection of a button may be made by clicking or touching depending on the type of the input 160.

In some embodiments, the tube voltage set button 151a may include an extra button to increase or decrease the tube voltage.

The tube current set button 151b may include an extra button to increase or decrease the tube current.

The tube current amount set button 151c may include an extra button to increase or decrease the amount of tube current.

Furthermore, an imaging position set button 151d to receive a setting of whether X-raying is performed on the stand 20 or on the table 10 or whether a portable X-ray detector is used, a patient size selection button 151e to receive a choice of a patient size, and a collimator set button 151f to receive setting of a size of the collimator may further be displayed.

Moreover, an AEC selection button 151g to receive a choice of an AEC sensor, a sensitivity set button 151h to receive setting of sensitivity, a density set button 151i to receive setting of a density, a grid selection button 151j to receive a choice of a grid, a filter selection button 151k to receive a choice of a filter, and a focus selection button 151r to receive a choice of a focal size may further be displayed in the setting window 151.

These buttons may be implemented in figures comprised of pictures, characters, symbols, etc., and the user may select a figure by moving the cursor to the figure and clicking it or touching the figure, and accordingly, an X-ray irradiation condition corresponding to the selected figure may be set.

Meanwhile, once an imaging protocol is selected, the X-ray irradiation conditions, such as a tube voltage, a tube current, an amount of tube current, and so forth, which are basic conditions matched with the selected imaging protocol, may be displayed in the respective display areas 151aa, 151bb, 151cc.

The storage 170 may match and store basic X-ray irradiation conditions for each imaging protocol. When an imaging protocol is selected, the controller 140 may search the storage 170 for basic X-ray irradiation conditions corresponding to the selected imaging protocol, and display the basic X-ray irradiation conditions in the respective display areas 151aa, 151bb, 151cc of the display 150.

The user may refer to the X-ray irradiation conditions displayed in the respective display area 151aa, 151bb, 151cc and adjust them to proper numerical values taking into account the state or size of the subject by increasing or decreasing the numerical values.

When a choice of a patient size is input, the X-ray irradiation conditions, such as a tube voltage, a tube current, an amount of tube current, and so forth, which are basic conditions matched with the selected size, may be displayed in the respective display areas 151aa, 151bb, 151cc.

For this, the storage 170 may match and store basic X-ray irradiation conditions for each patient size, and the basic X-ray irradiation conditions matched with the patient size may be stored differently for each imaging protocol.

When the user selects a patient size using the size selection button 151e, the controller 140 may search the storage 170 for basic X-ray irradiation conditions corresponding to the selected patient size, and display the basic X-ray irradiation conditions in the respective display areas 151aa, 151bb, 151cc of the display 150.

Even in this case, as described above, the user may refer to the X-ray irradiation conditions displayed in the respective display areas 151aa, 151bb, 151cc and adjust them to proper numerical values taking into account the state or size of the subject by increasing or decreasing the numerical values.

The aforementioned types or locations of the graphic objects displayed in the set window 151 are by way of example, and some of them may be omitted according to the designer's choice, and other graphic objects to change other settings may further be provided in an arrangement different from what is described above.

The input 160 may include a button to receive a command to start X-raying. For example, the button to receive a command to start X-raying may be implemented in the form of a remote control or a switch, which is separate from the workstation 180.

If the user inputs the command to start X-raying through the input 160 after setting the X-ray irradiation conditions through the setting window 151, X-raying is performed according to the set X-ray irradiation conditions.

In performing the X-raying, an effort is made to reduce a dose of radiation exposed to the patient. For this, it is important for the user to accurately know of the dose of radiation exposed to the patient taking place in a case that X-raying is performed according to the currently set X-ray irradiation conditions.

The conventional X-ray imaging apparatus provides no extra information about a dose of radiation except for the tube voltage, tube current, and amount of tube current. In that case, the user estimates a dose based on an amount of tube current (mAs).

FIG. 10 shows a table representing radiation doses depending on X-ray irradiation conditions;

Referring to FIG. 10, when the tube voltage is set to 80 kVp and the amount of tube current is set to 10.0 mAs, an actual dose is 0.72 mGy without the filter 112. When the tube voltage is increased to 83 kVp while the amount of tube current is decreased to 8.0 mAs, an actual dose is 0.62 mGy without the filter 112.

Since the conventional X-ray imaging apparatus does not provide information about an actual dose of radiation, the user may not accurately know of the dose and in light of the fact that the second case has a 20 percent lower amount of tube current than that of the first case, may only assume that a dose would be reduced (however, that the dose would be reduced by less than 20% because the tube voltage increases a little bit).

When the tube voltage is set to 76 kVp and the amount of tube current is set to 16.0 mAs, an actual does is 0.55 mGy when the filter 112 made of copper, which is about 0.1 mm thick, is used. In this case, the amount of tube current increases by about 60% as compared with the first case, and by 100% as compared with the second case, so the user may assume that a dose would increase as well. However, the dose in the third case is actually the lowest.

Specifically, if the user estimates a dose just based on the set tube voltage, tube current, and amount of tube current, it is difficult to know of an actual dose to which an influence of the filter is reflected. Accordingly, if a dose is estimated only based on the information and corresponding X-ray irradiation conditions are selected, it is difficult to select proper X-ray irradiation conditions in consideration of a dose of radiation exposure and the image quality.

In certain embodiments, the X-ray imaging apparatus 100 may guide the user to select proper X-ray irradiation conditions to minimize both a dose of radiation exposure and degradation of image quality by providing information about an actual dose, to which an influence of the filter is reflected, to the user. Examples in which the X-ray imaging apparatus 100 provides doses in accordance with an embodiment will now be described in detail with reference to accompanying drawings.

Figure 11:
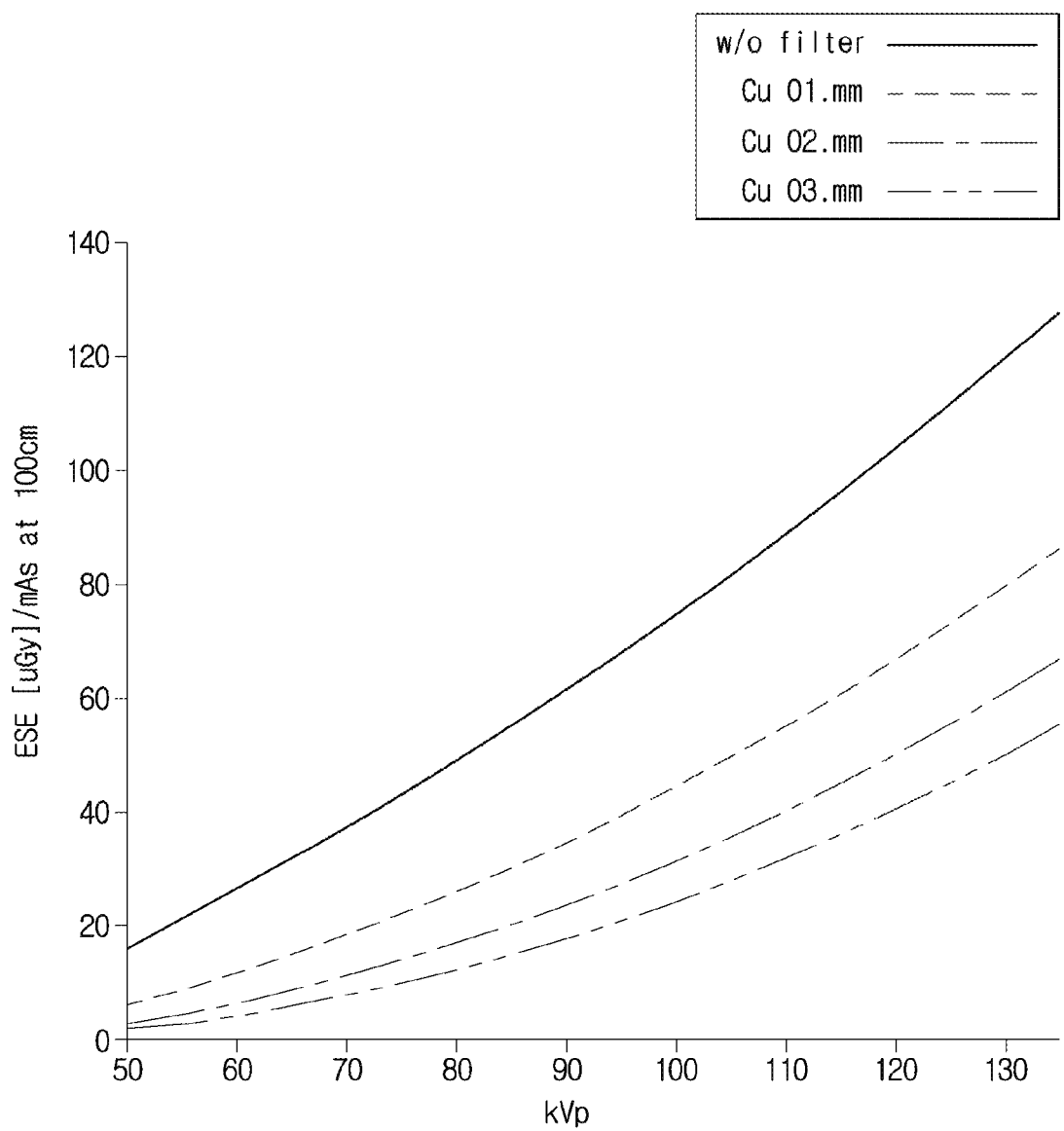
FIG. 11 illustrates a graph representing changes in radiation dose according to tube voltages and filter types/thickness.

FIG. 11 is a graph representing changes in radiation dose according to tube voltages and filter types/thickness.

As described above, the dose of radiation exposure may vary by an X-ray irradiation condition, such as the tube voltage, tube current, amount of tube current, filter type and thickness, etc. Once an X-ray irradiation condition is selected, the controller 140 obtains a dose of radiation exposure corresponding to the selected X-ray irradiation condition.

The dose of radiation exposure may be represented in such a value as entrance skin exposure (ESE), entrance surface dose (ESD), effective dose, dose-area product (DAP), etc. In this example, the ESE is used.

The storage 170 may store relationships between the dose (ESE) per amount of tube current (mAs) and the tube voltage for each type and filter thickness in advance. The dose per amount of tube current (mAs) may be obtained by experiment, simulation, etc.

For example, the dose (ESE) per amount of tube current (mAs) may be measured by differing the tube voltage, and the tube voltage and the measured dose (ESE) per amount of tube current (mAs) may be matched and stored in a table. Such relationships may be obtained by differing filter type and thickness. Even in the case that the filter is not used, relationships between the dose (ESE) per amount of tube current (mAs) and the tube voltage are obtained and stored.

In this embodiment, the filter whose influence is reflected may be the filter 112 arranged between the blade of the collimator 113 and the X-ray tube 111. Furthermore, if there is an extra filter such as a bow tie filter used to control the shape of X-raying, even for this filter, relationships between the dose (ESE) per amount of tube current (mAs) and the tube voltage of when this filter is used or not used may be obtained and stored in advance.

When a tube voltage and a filter are selected, the controller 140 searches the storage 170 for a dose E1 per amount of tube current (mAs) corresponding to the selected tube voltage and filter. Along with this, the controller 140 searches the storage 170 for a dose E2 per amount of tube current (mAs) corresponding to the selected tube voltage when no filter is used.

The controller 140 calculates a conversion ratio R1 using the dose E1 per amount of tube current (mAs) of when the filter is used and the dose E2 per amount of tube current (mAs) of when the filter is not used. The conversion ratio R1 may be calculated in the following equation 1:

$$R1 = E1/E2 \qquad (1)$$

The conversion ratio R1 is used to convert an amount of tube current selected by the user to an amount of tube current to which an influence of the filter is reflected, representing a ratio of a dose of X-rays that have not transmitted the filter and a dose of X-rays that have transmitted the filter.

The controller 140 calculates a converted amount of tube current M2 in the following equation 2 using the conversion ratio R1 and the selected amount of tube current M1:

$$M2 = M1 * R1 \qquad (2)$$

Furthermore, the controller 140 may calculate a dose E3, to which an influence of the filter is reflected, under a condition of the selected amount of tube current, using the dose E1 per amount of tube current when the filter is used and the selected amount of tube current M1.

$$E3 = M1 * E1 \qquad (3)$$

If the selected X-ray irradiation condition does not include usage of the filter, E1=E2. In the following embodiment, an occasion when the selected X-ray irradiation condition includes usage of a filter will be described.

FIGS. 12 to 18 show examples in which an X-ray imaging apparatus, in accordance with certain embodiments, displays information about radiation doses on a display, to which an influence of a filter is reflected.

The display 150 may display a parameter that represents a dose to which an influence of the filter is reflected in a numerical value or display the numerical value of the corresponding parameter in a diagram or an image.

Figure 12:
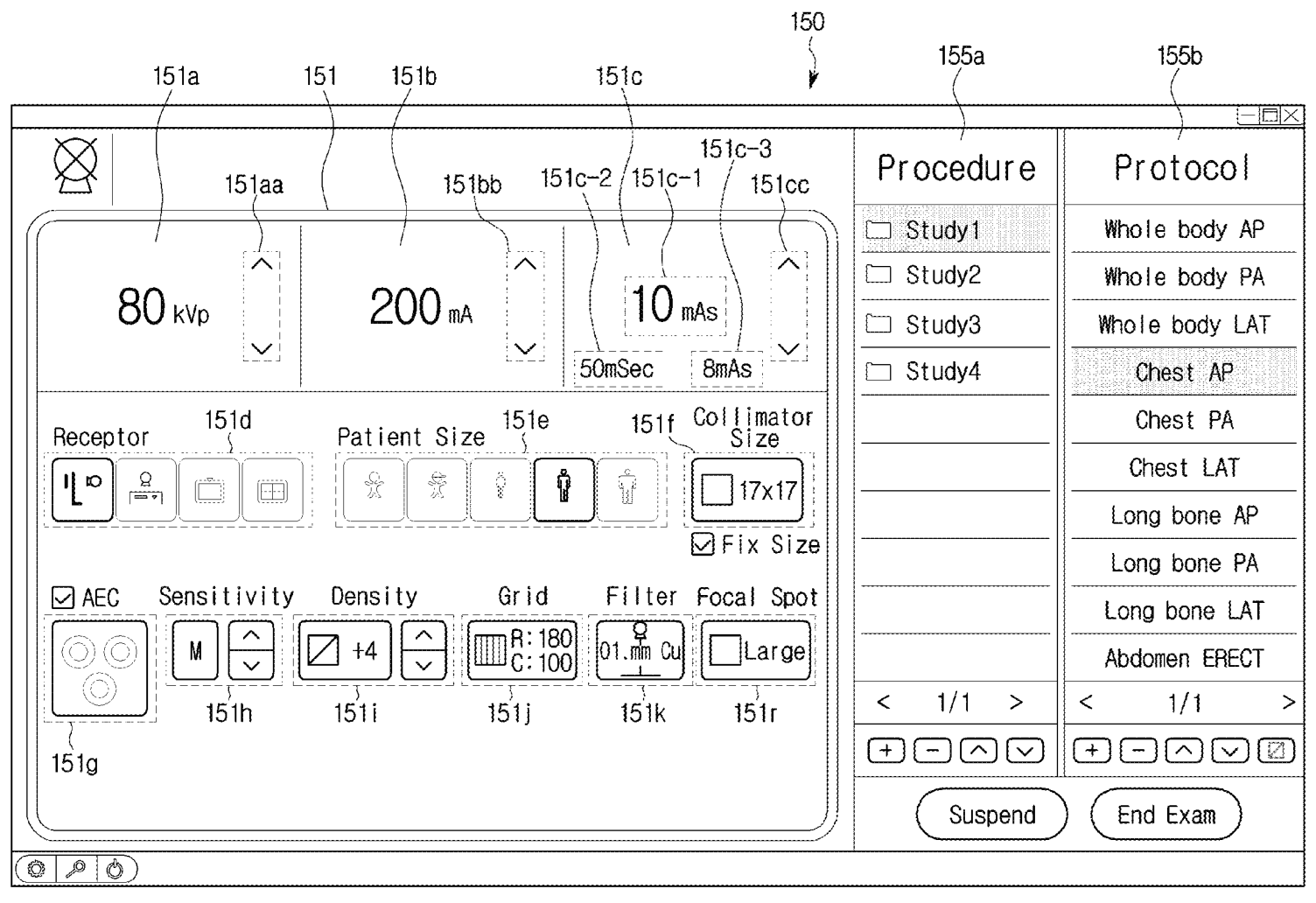

For example, as shown in FIG. 12, a currently selected amount of tube current 151c-1, exposure time 151c-2, and a converted amount of tube current 151c-3 may be displayed in numerical values in the tube current amount display area 151c. As described above, the converted amount of tube current 151c-3 is an amount of tube current to which an influence of the filter is reflected.

An occasion when a tube voltage of 80 kVp, a tube current of 200 mA, an amount of tube current of 10 mAs, and a copper filter of 0.1 mm are selected will be taken as an example. The X-ray irradiation conditions may be conditions directly selected by the user using the respective set buttons, or may be conditions basically matched with the selected imaging protocol and size of the subject.

The controller 140 searches the storage 170 for a dose per amount of tube current (mAs) corresponding to the selected tube voltage 80 kVp and the filter (copper of 0.1 mm) and a dose per amount of tube current (mAs) corresponding to the selected tube voltage 80 kVp and to an occasion when no filter is used.

The controller 140 may calculate the conversion ratio R1 using the equation 1 and obtain the converted amount of tube current M2 by substituting the conversion ratio R1 in the equation 1. If the conversion ratio R1 is 0.8, the converted amount of tube current M2 becomes 8 mAs, and the controller 140 may control the display 150 to display the converted amount of tube current 8 mAs as well in the tube current amount display area 151c.

The user checks the converted amount of tube current in a numerical value of 8 mAs, and may intuitively check how much a dose of radiation exposure would be when the copper filter of 0.1 mm is used.

Figure 13:
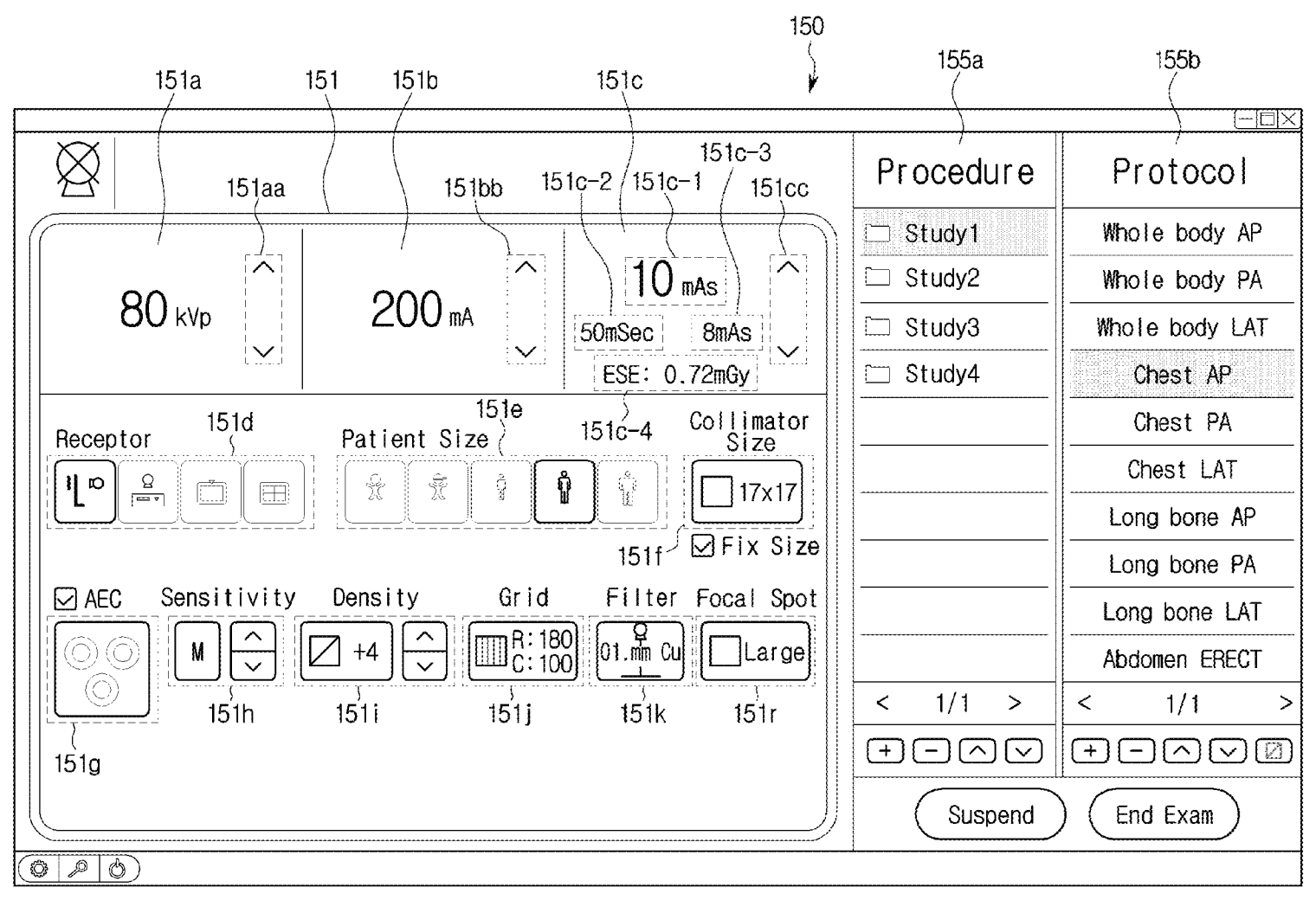

In another example, as shown in FIG. 13, it is also possible to represent a dose 151c-4 to which an influence of the filter is reflected in a numerical value. The controller 140 may search the storage 170 for a dose A1 per amount of tube current (mAs) corresponding to the selected X-ray irradiation condition, and may obtain a dose A3 to which an influence of the filter is reflected by multiplying the selected amount of tube current M1 by the searched for dose A1 per amount of tube current (mAs) according to the equation 3.

Figure 14:
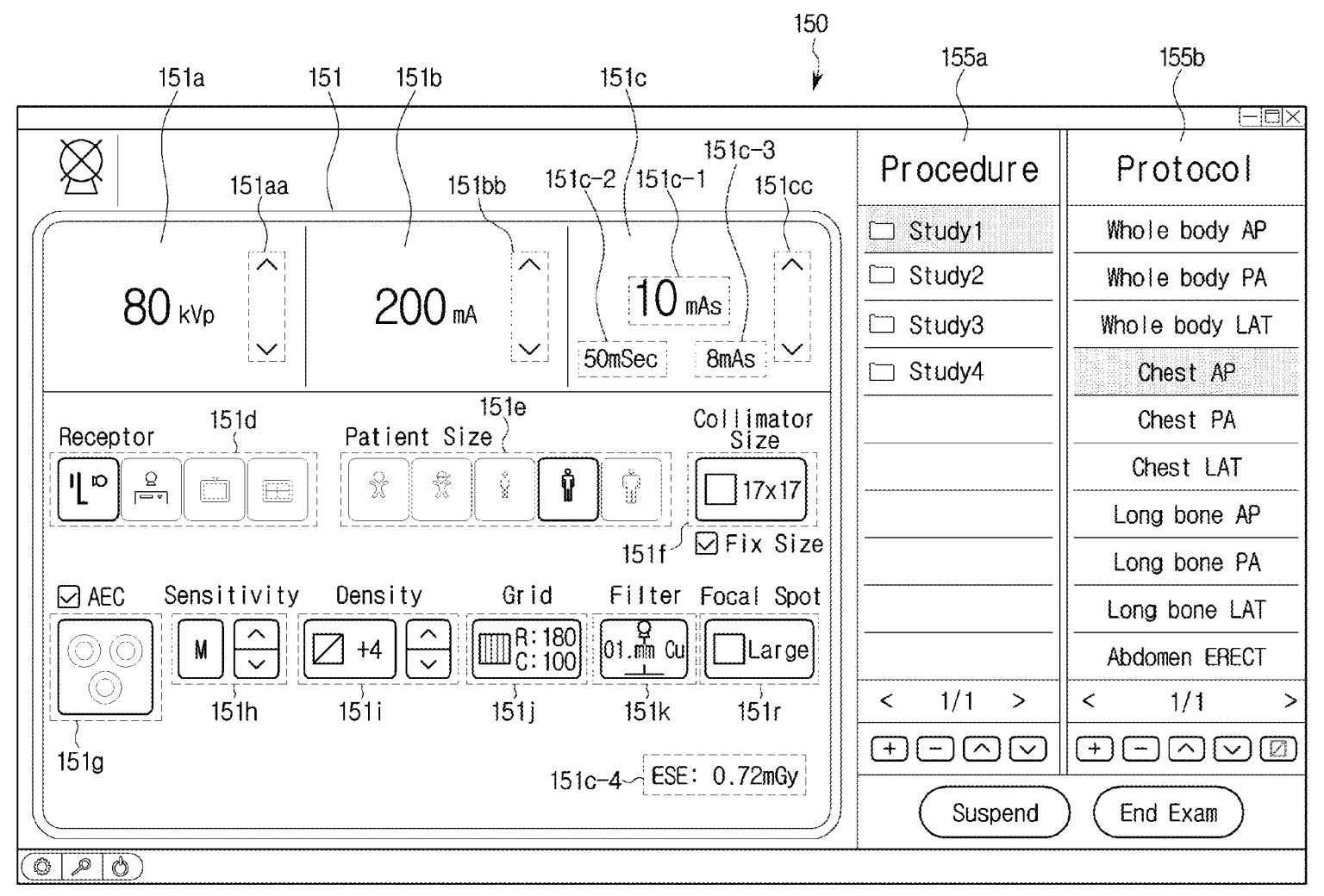

However, displaying the dose 151c-4 to which an influence of the filter is reflected is just an example. As shown in FIG. 14, it may also possible to display the dose 151c-4 in other area than the tube current amount display area 151c in the setting window 151.

Although both the converted amount of tube current 151c-3 and the dose 151c-4 to which an influence of the filter is reflected are represented in the examples of FIGS. 13 and 14, embodiments of the X-ray imaging apparatus 100 are not limited thereto. It is also possible to represent one of the converted amounts of tube current 151c-3 and the dose 151c-4 to which an influence of the filter is reflected.

Figure 15:
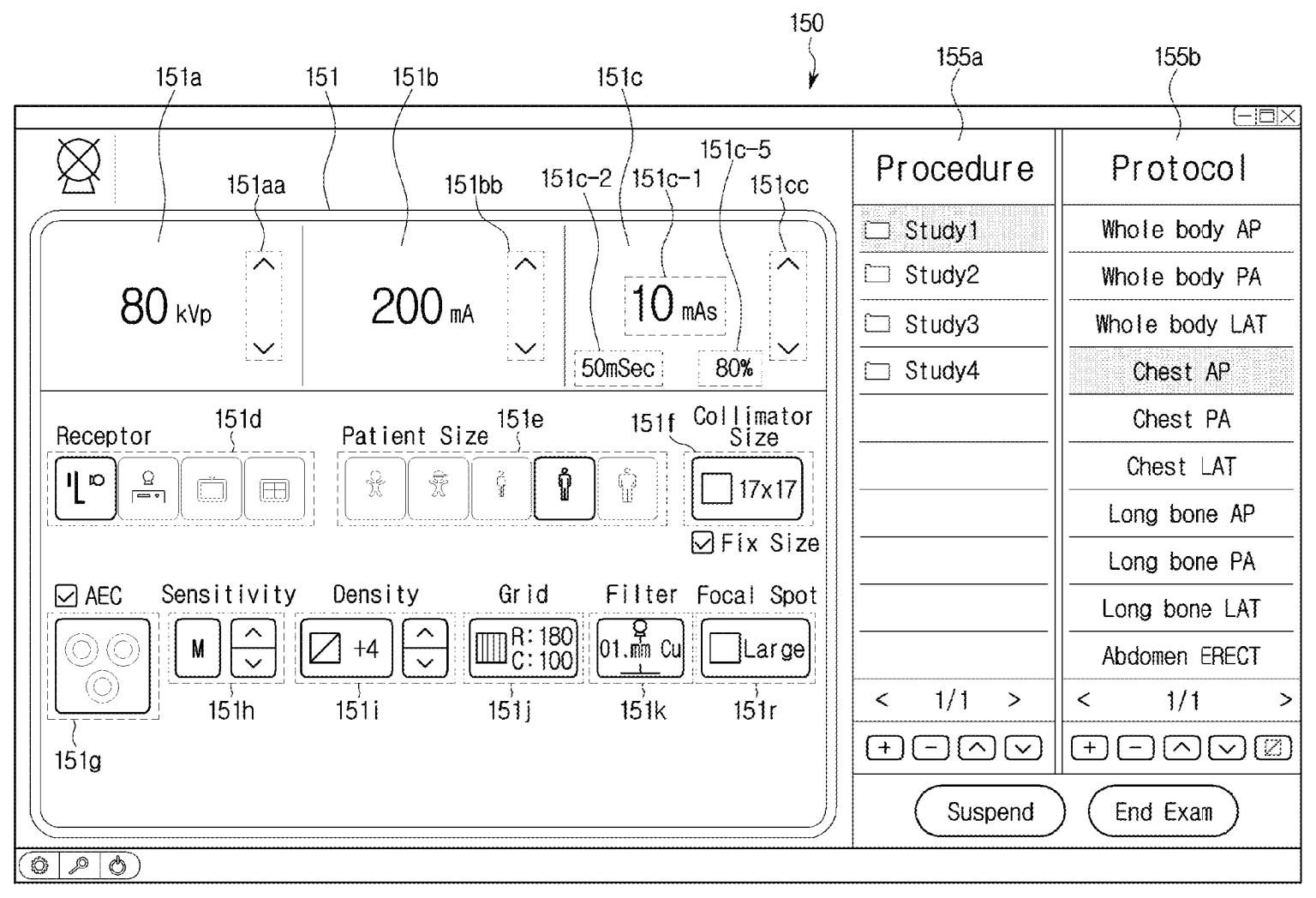

In another example, as shown in FIG. 15, it is also possible that the display 150 represents a conversion ratio 151c-5. When the conversion ratio 151c-5 is displayed, the user may intuitively know of a decrease in the dose due to use of the filter.

The conversion ratio 151c-5 may be represented as computed in the equation 1, or may be represented as a percentage as shown in FIG. 15.

Figure 16:
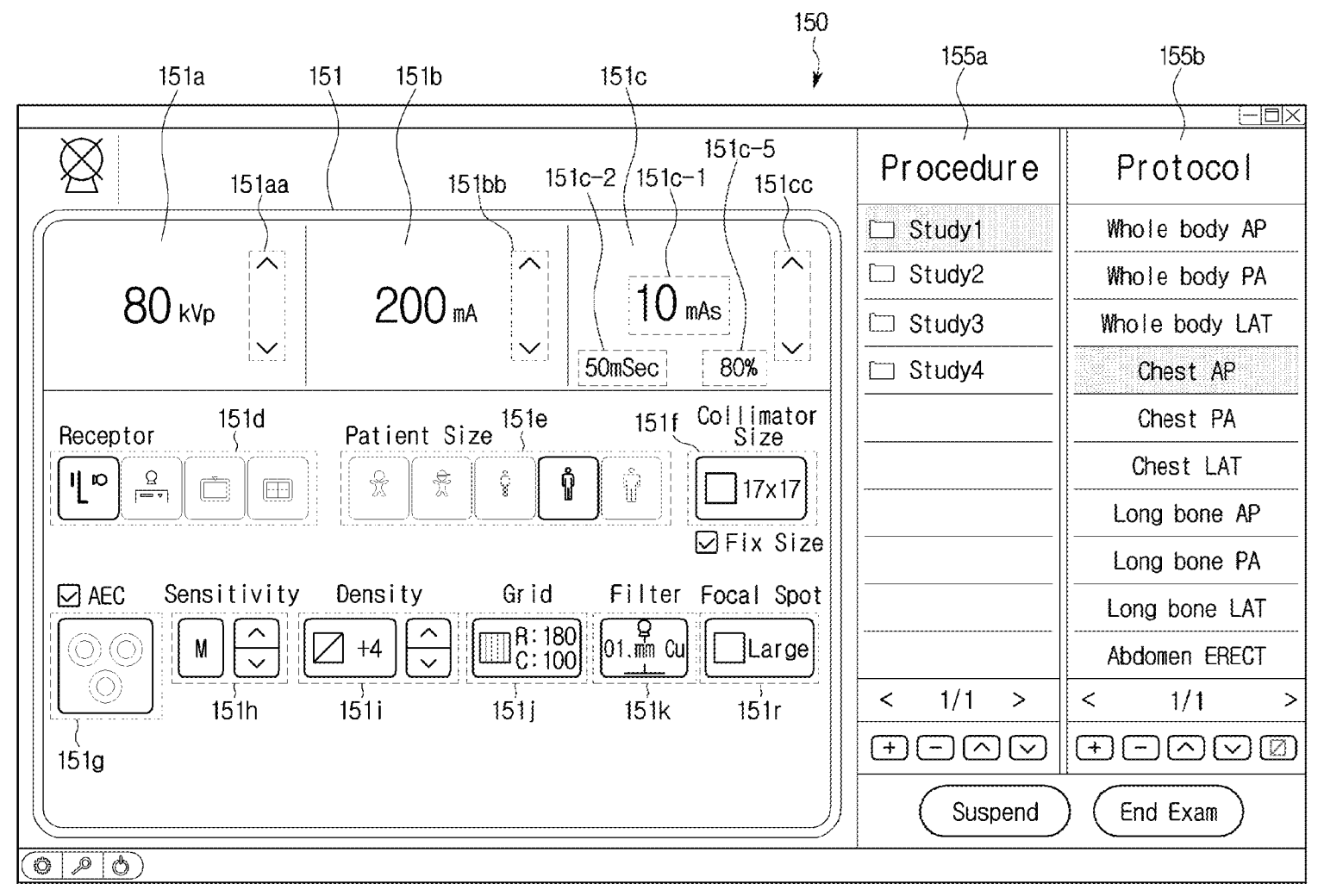
Figure 17:
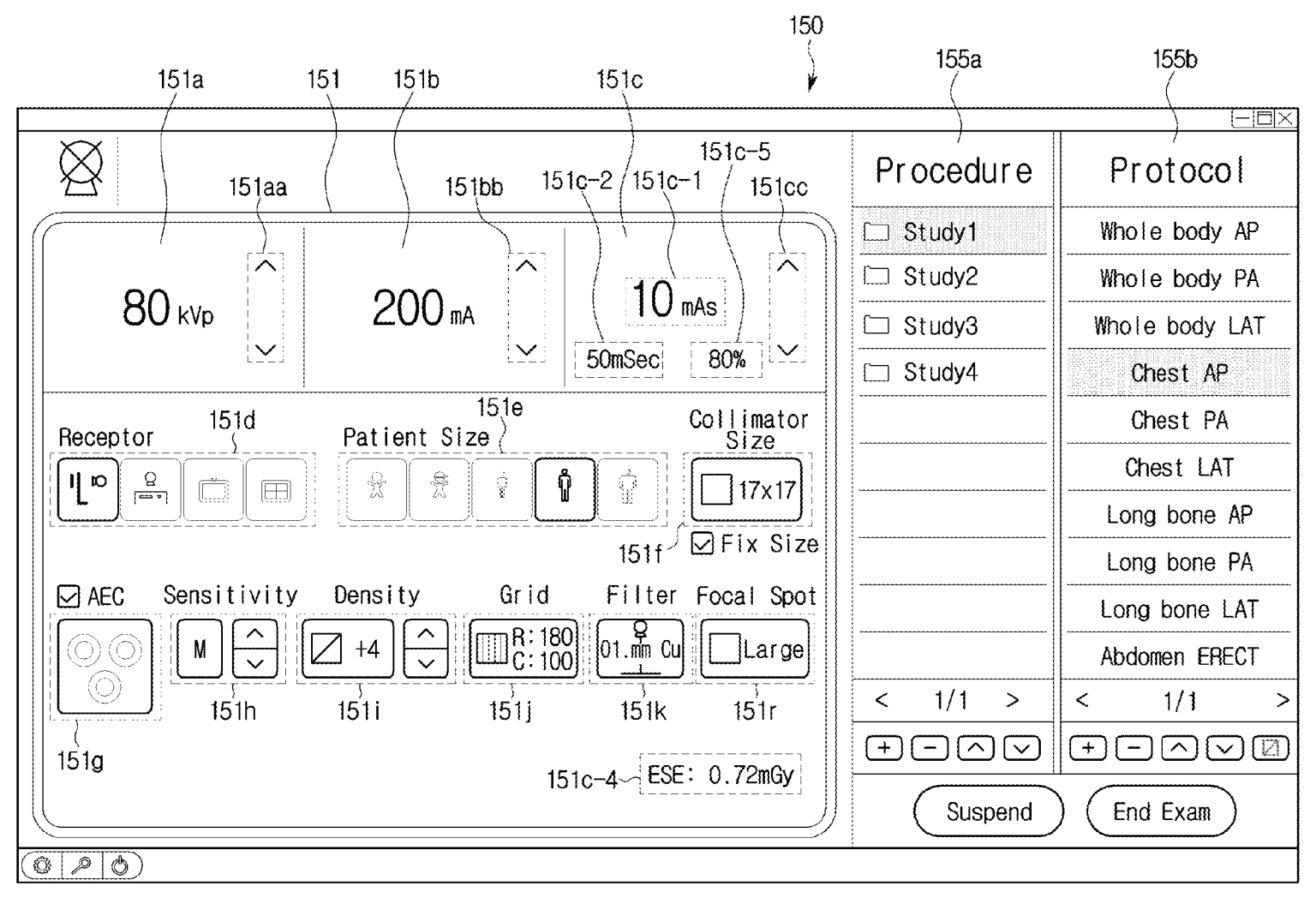

Similarly, in the case of representing the conversion ratio 151c-5, the dose 151c-4 to which an influence of the filter is reflected may also be represented, as shown in FIGS. 16 and 17. The user may receive information about a dose to which an influence of the filter is reflected from various aspects, thereby intuitively and accurately knowing of an actual dose of radiation exposure.

It is also possible to represent both the conversion ratio 151c-5 and the converted dose 151c-3.

Figure 18:
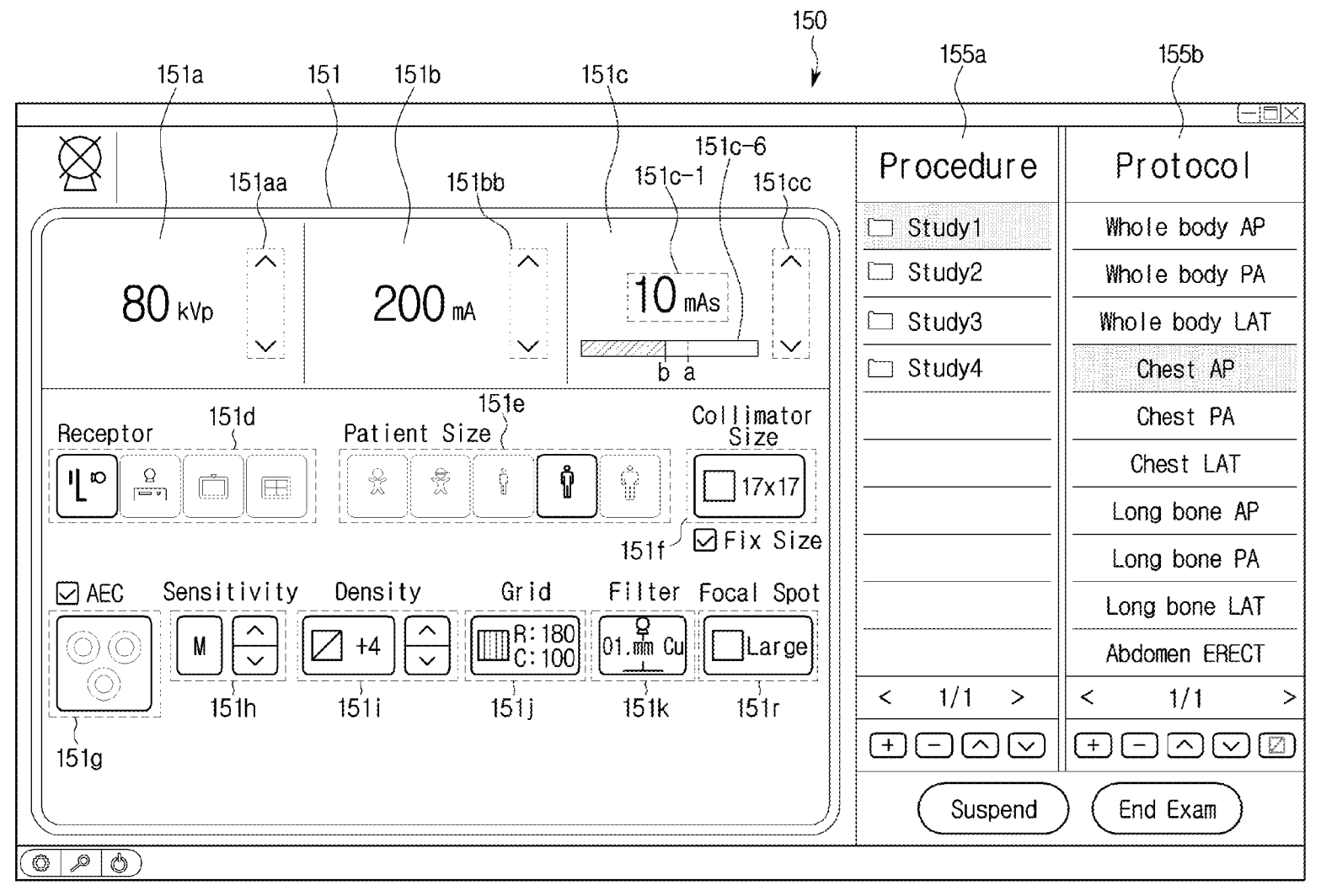

In another example, as shown in FIG. 18, it is also possible to show the relationship between a dose of when the filer is used and a dose of when the filter is not used in a diagram. Specifically, the dose of when the filter is used may be represented in the form of a bar 151c-6, and a ratio of the length of the bar representing the conversion ratio 151c-5 and the entire bar length may be adjusted to correspond to the conversion ratio 151c-5.

For example, in a case that the conversion ratio is 80%, the dose bar 151c-6 may be adjusted up to 80% of the length of the entire bar area.

Furthermore, if the user changes an X-ray irradiation condition, the length of the dose bar before the change and the length of the dose bar after the change may be represented together for the user to be able to intuitively know of a change of the dose according to the change in the X-ray irradiation condition.

A control method of an X-ray imaging apparatus in accordance with an embodiment of the present disclosure will now be described. The control method of an X-ray imaging apparatus may use the X-ray imaging apparatus 100. Therefore, the above description with respect to FIGS. 1 to 18 may also be applied to the embodiment of the control method of X-ray imaging apparatus without being specifically told.

Figure 19:
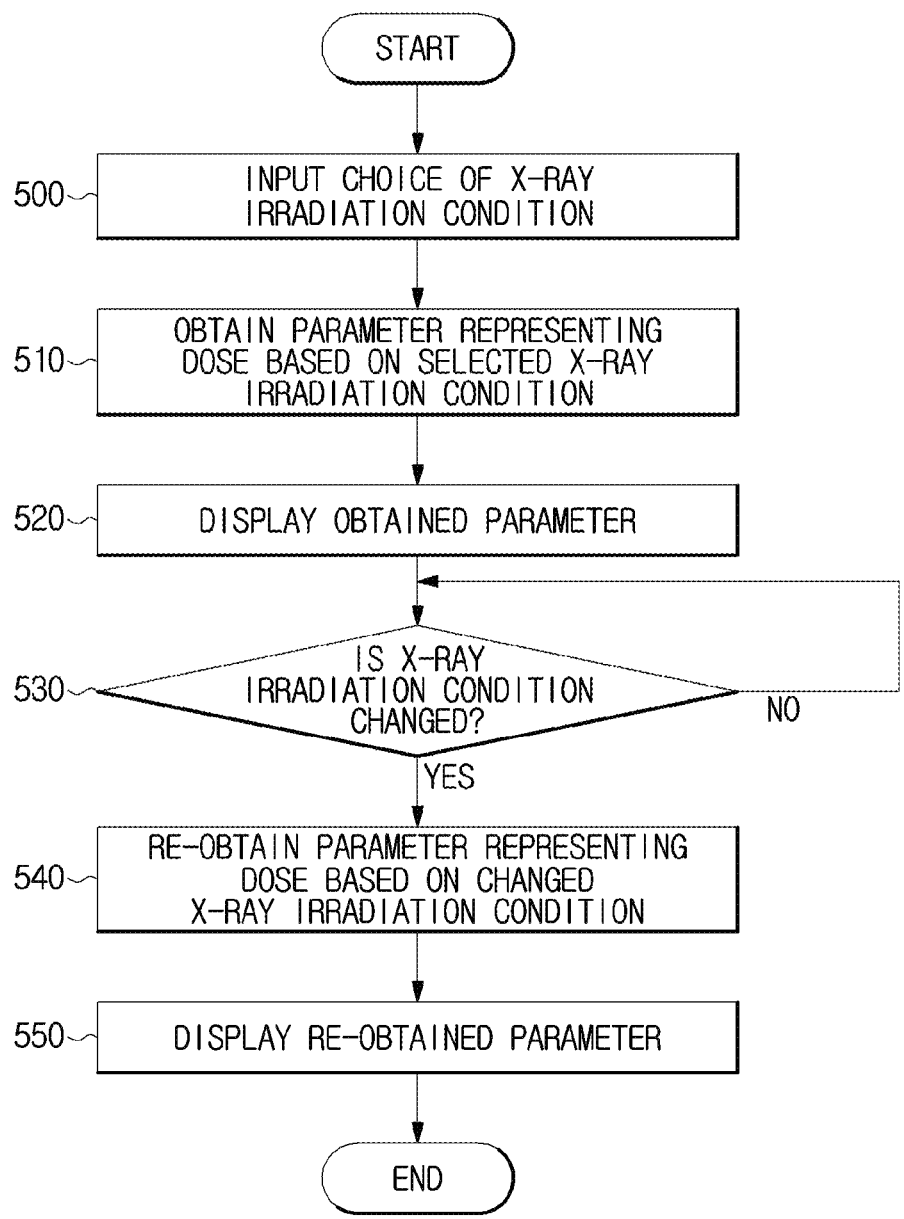
FIG. 19 illustrates a flowchart of a control method of an X-ray imaging apparatus, according to an embodiment of the present disclosure.

FIG. 19 illustrates a flowchart of a control method of an X-ray imaging apparatus, according to an embodiment of the present disclosure.

Referring to FIG. 19, a choice of an X-ray irradiation condition is received, in 500. The selected X-ray irradiation condition may be conditions directly set by the user using the set buttons provided to correspond to the respective X-ray irradiation conditions, or may be conditions basically matched with an imaging protocol and size of the subject.

A parameter that represents a dose is obtained based on the selected X-ray irradiation condition, in 510. The parameter that represents a dose includes at least one of a converted amount of tube current to which an influence of the filter is reflected, a dose calculated from a conversion ratio, and the conversion ratio. The conversion ratio refers to a ratio of a dose corresponding to the selected X-ray irradiation condition and a dose of when the filter is not used under the same condition.

The obtained parameter is displayed on the display 150. As shown in FIGS. 12 to 18, the calculated numerical value may be displayed along with the amount of tube current 151c-1 in a portion of the tube current amount display area 151c, or may be displayed in an area of the setting window 151 other than the tube current amount display area 151c, or may be shown in a diagram. There are no limitations on how to represent the parameter.

When the X-ray irradiation condition is changed, in 530, a parameter that represents a dose based on the changed X-ray irradiation condition is obtained again, in 540. If the user changes X-ray irradiation conditions using various buttons provided in the setting window 151, the controller 140 may recalculate the parameter that represents a dose by reflecting the change in real time.

The parameter obtained again is displayed on the display, in 550. This may allow the user to intuitively check the changing dose according to the change in X-ray irradiation condition and to select a proper X-ray irradiation condition considering both the dose of radiation exposure and the X-ray image quality.

Figure 20:
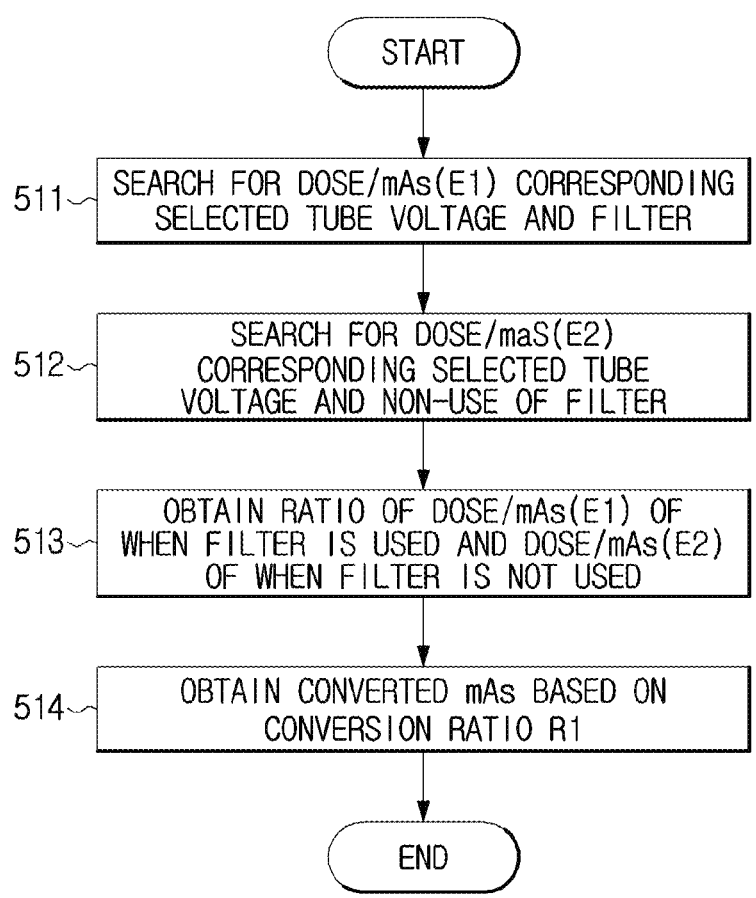
FIG. 20 illustrates a flowchart of an example of obtaining a parameter that represents an radiation dose in a control method of an X-ray imaging apparatus, according to an embodiment of the present disclosure.

FIG. 20 illustrates a flowchart of an example of calculating a parameter that represents a dose in a control method of an X-ray imaging apparatus, according to an embodiment of the present disclosure.

Referring to FIG. 20, the dose E1 per amount of tube current corresponding to the selected tube voltage and filter is searched for from the storage 170. For this, relationships between dose per amount of tube current (mAs) and tube voltage may be stored in advance for each filter type and thickness. The dose per amount of tube current (mAs) may be obtained by experiment, simulation, etc.

For example, the dose per amount of tube current (mAs) may be measured by differing the tube voltage, and the tube voltage and the measured dose per amount of tube current (mAs) may be matched and stored in a table. Such relationships may be obtained by differing filter type and thickness. Even in the case that the filter is not used, relationships between the dose per amount of tube current (mAs) and the tube voltage are obtained and stored.

The dose E2 per amount of tube current corresponding to a selected tube voltage and non-use of filter is searched for, in 512. As described above, since the storage 170 stores both the dose of when the filter is used and the dose of when the filter is not used under the same tube voltage condition, the controller 170 may search the storage 170 for the both information.

A ratio of the dose E1 per amount of tube current in a case of using the filter and the dose E2 per amount of tube current when not using the filter, that is, the conversion ratio R1, is obtained, in 513. The controller 140 may calculate the conversion ratio R1=E1/E2 based on the equation 1.

Based on the conversion ratio R1, a converted amount of tube current is obtained, in 514. The controller 140 calculates a converted amount of tube current M2 by substituting the conversion ratio R1 and the selected amount of tube current M1 in the equation 2. The converted amount of tube current M2 represents an amount of tube current to which an influence of the filter is reflected.

Figure 21:
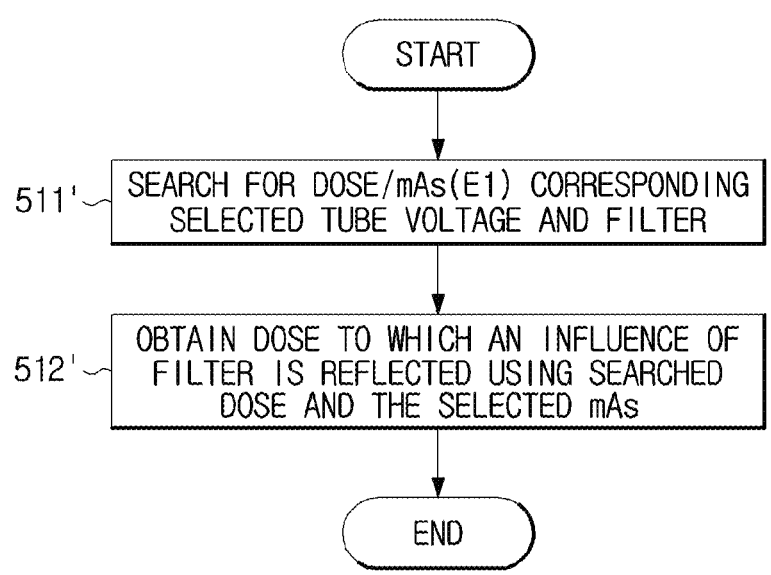
FIG. 21 illustrates a flowchart of an example of obtaining a parameter that represents an radiation dose in a control method of an X-ray imaging apparatus, according to another embodiment of the present disclosure.

FIG. 21 illustrates a flowchart of an example of calculating a parameter that represents a dose in a control method of an X-ray imaging apparatus, according to another embodiment of the present disclosure.

Referring to FIG. 21, the dose E1 per amount of tube current corresponding to a selected tube voltage and filter is searched for from the storage 170, in 511', and the dose M2 to which an influence of the filter is reflected is obtained using the searched for dose E1, in 512'. The controller 140 may calculate the dose M2 to which the influence of the filter is reflected according to the equation 3.

The calculated dose or amount of tube current may be displayed on the display 150 in various ways. Furthermore, the conversion ratio R1 may be displayed. The conversion ratio R1 may be represented as a percentage.

The dose, amount of tube current, or conversion ratio may be represented by direct numerical values in the tube current display area 151c or in the other area, or may be schematized into diagrams or images.

Furthermore, when an X-ray irradiation condition is changed and a newly calculated parameter is displayed, a relationship between the new parameter and the old parameter before the change may also be displayed. For example, as shown in FIG. 18, the length a of a dose bar before the change and the length b of a dose bar after the change may be displayed together. In this case, the user may intuitively know of a change of the dose that varies by the change in X-ray irradiation condition.

The control method of X-ray imaging apparatus according to the embodiments of the present disclosure may be implemented in program instructions which are executable by various computing means and recorded in computer-readable media.

The computer-readable media may include program instructions, data files, data structures, etc., separately or in combination. For example, the computer-readable recording media may include, no matter whether it is erasable or rewritable, volatile or non-volatile storage devices, such as random access memory (RAM), read only memory (ROM), magnetic storage media (for example, floppy disks, hard disks, etc.), and optical recording media (such as, CD-ROMs, or DVDs). The computer-readable recording medium may also be distributed over network coupled computer systems so that the computer readable code is stored and executed in a distributed fashion. This media may be read by the computer, stored in the memory, and executed by the processor.

The computer-readable medium that may be included in a portable terminal may be an example of a machine-readable readable recording medium suitable for storing a program or programs having instructions that implement the embodiments of the present disclosure. The program instructions recorded on the computer-readable media may be designed and configured specially for the present disclosure, or may be well-known to people having ordinary skill in the art of computer software.

According to the embodiments of an X-ray imaging apparatus and control method thereof, information about an actual dose to which an influence of the filter is reflected is provided for the user to be able to intuitively know of the dose under a corresponding X-ray irradiation condition. This may allow setting of a proper X-ray irradiation condition taking into account both a dose of radiation exposure and quality of X-ray image.

According to embodiments of the present disclosure, an X-ray imaging apparatus and control method thereof, may guide the user to intuitively recognize an actual dose of X-rays and select a proper dose, ultimately a condition for a low dose of X-rays by providing the user with information about an actual dose of X-rays to which an X-ray filter effect is reflected.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. An X-ray imaging apparatus comprising:
an X-ray source configured to generate and irradiate X-rays according to X-ray irradiation conditions including a tube voltage, a tube current, an exposure time, and a filter;
a display configured to provide a graphic user interface to receive a selection about the X-ray irradiation conditions; and
a controller configured to:
calculate a conversion ratio of a dose of x-rays that have not transmitted the filter to a dose of X-rays that have transmitted the filter,
calculate, based on the conversion ratio, a parameter that represents a dose of radiation, to which an influence of the filter is reflected, based on a selected X-ray irradiation conditions and control the display to display the parameter,
wherein the parameter comprises at least one of a converted amount of tube current corresponding to X-rays that have transmitted the filter, an amount of dose of X-rays that have transmitted the filter, or the conversion ratio,
wherein the converted amount of tube current is given by an amount of a selected tube current multiplied by the conversion ratio, wherein the amount of dose X-rays that have transmitted the filter is given by the amount of the selected tube current multiplied by a dose per amount of tube current when the selected filter is used, and wherein the controller is configured to obtain the conversion ratio of the dose of X-rays that have not transmitted the filter to the dose of X-rays that have transmitted the filter, based on the dose per amount of tube current corresponding to the selected X-ray irradiation conditions and the dose per amount of tube current corresponding to an occasion when the filter is not used in the selected X-ray irradiation conditions.

2. The X-ray imaging apparatus of claim 1, wherein the display is configured to display the parameter in a numerical value, or a diagram or image representing the numerical value.

3. The X-ray imaging apparatus of claim 1, further comprising:
a storage configured to store relationships between dose per amount of tube current (mAs) and tube voltage by differing types or thickness of the filter.

4. The X-ray imaging apparatus of claim 3, wherein the controller is configured to search the storage for a dose per amount of tube current corresponding to the selected X-ray irradiation conditions, when the selection of the X-ray irradiation conditions is input.

5. The X-ray imaging apparatus of claim 4, wherein the controller is configured to additionally search for a dose per amount of tube current corresponding to the occasion when no filter is used in the selected X-ray irradiation conditions.

6. The X-ray imaging apparatus of claim 1, wherein the controller is configured to when at least one of an imaging protocol or a size of a subject is selected, control the display to display a basic X-ray irradiation condition corresponding to the selected at least one of the imaging protocol or the size of the subject.

7. The X-ray imaging apparatus of claim 6, wherein the controller is configured to obtain a parameter that represents a dose to which an influence of the filter is reflected based on the basic X-ray irradiation condition.

8. The X-ray imaging apparatus of claim 1, wherein the controller is configured to re-obtain a parameter that represents a dose of radiation, to which an influence of the filter is reflected, whenever a selection of the X-ray irradiation condition is changed, and control the display to display the parameter.

9. A control method of an X-ray imaging apparatus, the method comprising:
providing a graphic user interface configured to receive a selection of an X-ray irradiation conditions including a tube voltage, a tube current, exposure time, and a filter;
calculating a conversion ratio of a dose of x-rays that have not transmitted the filter to a dose of X-rays that have transmitted the filter,
calculating, based on the conversion ratio, a parameter that represents a dose to which an influence of the filter is reflected based on a selected X-ray irradiation condition; and
displaying the parameter on a display,
wherein the parameter comprises at least one of a converted amount of tube current corresponding to X-rays that have transmitted the filter, an amount of dose of X-rays that have transmitted the filter, or the conversion ratio,
wherein the converted amount of tube current is given by an amount of a selected tube current multiplied by the conversion ratio,
wherein the amount of dose X-rays that have transmitted the filter is given by the amount of the selected tube current multiplied by a dose per amount of tube current of when the selected filter is used,
wherein the calculating of the parameter comprises:
obtaining the conversion ratio of the dose of X-rays that have not transmitted the filter to the dose of X-rays that have transmitted the filter, based on the dose per amount of tube current corresponding to the selected X-ray irradiation conditions and the dose per amount of tube current corresponding to an occasion when the filter is not used in the selected X-ray irradiation conditions.

10. The method of claim 9, wherein the displaying of the parameter on the display comprises:
displaying the parameter in a numerical value, or a diagram or image representing the numerical value.

11. The method of claim 9, further comprising: storing relationships between dose per amount of tube current (mAs) and tube voltage by differing types or thickness of the filter in a storage.

12. The method of claim 11, wherein the obtaining of the parameter comprises:
searching the storage for a dose per amount of tube current corresponding to the selected X-ray irradiation condition, when the selection of the X-ray irradiation condition is input.

13. The method of claim 12, wherein the obtaining of the parameter comprises:
searching for a dose per amount of tube current corresponding to the occasion when no filter is used in the selected X-ray irradiation condition.

* * * * *